(12) United States Patent
Iida et al.

(10) Patent No.: US 11,697,106 B2
(45) Date of Patent: Jul. 11, 2023

(54) POROUS CARBON MATERIAL COMPOSITES AND THEIR PRODUCTION PROCESS, ADSORBENTS, COSMETICS, PURIFICATION AGENTS, AND COMPOSITE PHOTOCATALYST MATERIALS

(71) Applicant: Sony Corporation, Tokyo (JP)

(72) Inventors: Hironori Iida, Kanagawa (JP); Seiichiro Tabata, Kanagawa (JP); Shinichiro Yamada, Kanagawa (JP); Tsutomu Noguchi, Kanagawa (JP); Shun Yamanoi, Kanagawa (JP)

(73) Assignee: SONY CORPORATION, Tokyo (JP)

( * ) Notice: Subject to any disclaimer, the term of this patent is extended or adjusted under 35 U.S.C. 154(b) by 394 days.

(21) Appl. No.: 17/066,149

(22) Filed: Oct. 8, 2020

(65) Prior Publication Data

US 2021/0023535 A1 Jan. 28, 2021

Related U.S. Application Data

(60) Division of application No. 15/876,382, filed on Jan. 22, 2018, now abandoned, which is a continuation of
(Continued)

(30) Foreign Application Priority Data

Sep. 29, 2008 (JP) .................................. 2008-250679
Aug. 7, 2009 (JP) .................................. 2009-184350

(51) Int. Cl.
*B01J 21/18* (2006.01)
*A61K 8/19* (2006.01)
(Continued)

(52) U.S. Cl.
CPC .................. *B01J 21/18* (2013.01); *A61K 8/19* (2013.01); *A61K 8/9711* (2017.08); *A61K 8/9739* (2017.08); *A61K 8/9741* (2017.08); *A61K 8/9789* (2017.08); *A61K 8/9794* (2017.08); *A61K 47/06* (2013.01); *A61L 9/01* (2013.01); *A61L 9/205* (2013.01); *A61Q 19/08* (2013.01); *B01D 53/02* (2013.01); *B01D 53/885* (2013.01); *B01J 20/02* (2013.01); *B01J 20/0211* (2013.01); *B01J 20/0229* (2013.01); *B01J 20/0244* (2013.01); *B01J 20/06* (2013.01); *B01J 20/20* (2013.01); *B01J 20/2803* (2013.01); *B01J 20/28009* (2013.01); *B01J 20/28011* (2013.01); *B01J 20/28057* (2013.01); *B01J 20/28069* (2013.01); *B01J 20/28083* (2013.01); *B01J 20/3204* (2013.01); *B01J 20/3236* (2013.01); *B01J 35/004* (2013.01); *B05D 1/18* (2013.01); *B05D 3/0473* (2013.01); *B05D 3/0486* (2013.01); *B05D 3/104* (2013.01); *C01B 32/00* (2017.08); *C01B 32/30* (2017.08); *C01B 32/318* (2017.08); *C02F 1/283* (2013.01); *C02F 1/288* (2013.01); *C25D 3/56* (2013.01); *H01B 1/04* (2013.01); *H01F 1/01* (2013.01); *H01L 31/0264* (2013.01); *A61K 2800/413* (2013.01); *A61K 2800/522* (2013.01); *A61K 2800/56* (2013.01); *B01D 2253/102* (2013.01); *B01D 2253/306* (2013.01); *B01D 2253/311* (2013.01); *B01D 2255/104* (2013.01); *B01D 2255/106* (2013.01); *B01D 2255/1021* (2013.01); *B01D 2255/1023* (2013.01); *B01D 2255/20761* (2013.01); *B01D 2255/702* (2013.01); *B01D 2255/802* (2013.01); *B01D 2255/9205* (2013.01);
(Continued)

(58) Field of Classification Search
CPC ...... B01J 21/18; B01J 20/02; B01J 20/28009; B01J 20/28011; A61K 8/19; A61K 8/9711; A61K 8/9739; A61K 8/9741; A61K 8/9789; A61K 8/9794; A61L 9/205; B01D 53/02; B01D 53/885
See application file for complete search history.

(56) References Cited

U.S. PATENT DOCUMENTS 1,729,162 A    9/1929  Coates
4,466,932 A *  8/1984  Koyama .................. C08G 8/04
                                                  264/29.4
(Continued)

FOREIGN PATENT DOCUMENTS

EP    2060535      5/2009
JP    09-296171    11/1997
(Continued)

OTHER PUBLICATIONS

Guo et al. (Dyes and Pigments 66, 2005, 123-128, IDS (Year: 2005).*
(Continued)

*Primary Examiner* — Anna R Falkowitz
(74) *Attorney, Agent, or Firm* — Dentons US LLP

(57) ABSTRACT

A porous carbon material composite formed of a porous carbon material and a functional material and equipped with high functionality. The porous carbon material composite is formed of (A) a porous carbon material obtainable from a plant-derived material having a silicon (Si) content of 5 wt % or higher as a raw material; and (B) a functional material adhered on the porous carbon material, and has a specific surface area of 10 m²/g or greater as determined by the nitrogen BET method and a pore volume of 0.1 cm³/g or greater as determined by the BJH method and MP method.

18 Claims, 19 Drawing Sheets

Related U.S. Application Data application No. 15/140,569, filed on Apr. 28, 2016, now abandoned, which is a division of application No. 12/741,967, filed as application No. PCT/JP2009/066737 on Sep. 28, 2009, now abandoned.

(51) Int. Cl.

| | | |
|---|---|---|
| *A61L 9/01* | (2006.01) | |
| *A61K 8/9711* | (2017.01) | |
| *A61K 8/9739* | (2017.01) | |
| *A61K 8/9794* | (2017.01) | |
| *A61K 47/06* | (2006.01) | |
| *A61Q 19/08* | (2006.01) | |
| *B01D 53/02* | (2006.01) | |
| *B01D 53/88* | (2006.01) | |
| *B01J 20/02* | (2006.01) | |
| *B01J 20/06* | (2006.01) | |
| *B01J 20/20* | (2006.01) | |
| *B01J 20/28* | (2006.01) | |
| *B01J 20/32* | (2006.01) | |
| *C02F 1/28* | (2023.01) | |
| *C01B 32/00* | (2017.01) | |
| *C01B 32/20* | (2017.01) | |
| *C01B 32/318* | (2017.01) | |
| *C25D 3/56* | (2006.01) | |
| *C25D 7/00* | (2006.01) | |
| *H01B 1/04* | (2006.01) | |
| *H01L 31/0264* | (2006.01) | |
| *A61L 9/20* | (2006.01) | |
| *B01J 35/00* | (2006.01) | |
| *C01B 32/30* | (2017.01) | |
| *A61K 8/9741* | (2017.01) | |
| *A61K 8/9789* | (2017.01) | |
| *B05D 1/18* | (2006.01) | |
| *B05D 3/04* | (2006.01) | |
| *B05D 3/10* | (2006.01) | |
| *H01F 1/01* | (2006.01) | |
| *B01J 21/06* | (2006.01) | |
| *B01J 35/10* | (2006.01) | |
| *B01J 37/02* | (2006.01) | |
| *C02F 103/00* | (2006.01) | |

(52) U.S. Cl.
CPC ..... *B01D 2255/9207* (2013.01); *B01J 21/063* (2013.01); *B01J 35/1014* (2013.01); *B01J 35/1038* (2013.01); *B01J 37/0203* (2013.01); *B01J 2220/485* (2013.01); *C02F 2103/007* (2013.01); *Y10T 428/249969* (2015.04)

(56) References Cited

U.S. PATENT DOCUMENTS

| | | | | |
|---|---|---|---|---|
| 5,338,462 A | * | 8/1994 | Abe | ............ B01J 21/18 |
| | | | | 210/757 |
| 5,834,138 A | * | 11/1998 | Yamada | ............ H01M 4/583 |
| | | | | 429/231.6 |
| 6,114,280 A | | 9/2000 | Stephens | |
| 6,680,277 B2 | * | 1/2004 | Morikawa | ............ B01J 35/002 |
| | | | | 502/200 |
| 2006/0057355 A1 | * | 3/2006 | Suzuki | ............ B82Y 30/00 |
| | | | | 428/408 |
| 2006/0148645 A1 | | 7/2006 | Schonfeld et al. | |
| 2007/0123420 A1 | | 5/2007 | Hayashi et al. | |
| 2012/0028796 A1 | | 2/2012 | Tabata et al. | |
| 2013/0209799 A1 | | 8/2013 | Iida et al. | |
| 2013/0250398 A1 | | 9/2013 | Takanashi et al. | |
| 2013/0310253 A1 | | 11/2013 | Tabata et al. | |

FOREIGN PATENT DOCUMENTS

| | | |
|---|---|---|
| JP | 2000-211910 | 8/2000 |
| JP | 2003-080061 | 3/2003 |
| JP | 2005-139102 | 6/2005 |
| JP | 2006-016221 | 1/2006 |
| JP | 2006-128133 | 5/2006 |
| JP | 2006-167694 | 6/2006 |
| JP | 2007-284337 | 11/2007 |
| WO | WO/2007/074956 | 7/2007 |

OTHER PUBLICATIONS

Della et al. (Materials Letters 57 (2002) 818-821) (Year: 2002).*
Guo et al., Use of Rice Husk-Based Porous Carbon for Absorption of Rhodamine B from Aqueous Solutions, Dyes and Pigments, vol. 66 (2005) pp. 123-128.
Gue et al.,(Dyes and Pigments vol. 66 (2005) pp. 123-128 IDS).
Baker et al., Carbon, Activated, Kirk-Othmer Encyclopedia of Chemical Technology, vol. 4, (2003) pp. 741-761.
Della, et al., Rice husk ash as an alternative source for active silica production, Material Letters vol. 57 (Dec. 2002) pp. 818-821.
Chinese Office Action issued in connection with related Chinese Patent Application No. 201610726324.2 dated Sep. 30, 2018 with English translation.
Liu, Yazi, et al., "Low-temperature preparation and microwave photocatalytic activity study by TiO2-mounted activated carbon", Journal of Hazardous Materials vol. 142 (2007), pp. 208-215.
European Summons to attend oral proceedings pursuant to Rule 115 (1) EPC issued in connection with related European Application No. 09816237.3 dated Oct. 25, 2018.
Chinese Office Action issued in connection with related Chinese Patent Application No. 201610726324.2 dated May 5, 2019 with English translation.
European Patent Office Examination dated Jan. 25, 2018 issued in corresponding European Patent Application No. 09816237.3.
Extended European Search Report issued in connection with related European Patent Application No. 20167224.3 dated Jul. 1, 2020.
Lu et al., "Application of polyol process to prepare AC-supported nanocatalyst for VOC oxidation", Applied Catalysis a: General, Elsevier Science, Amsterdam, NL, vol. 325, No. 1, dated May 10, 2007 pp. 163-174.
Ku et al., Hydrogen generation from hydrolysis of alkaline sodium borohydride solution using Pt/C catalyst:, Catalysis Communications, Elsevier Science, Amsterdam, NL, vol. 8, No. 11,dated Mar. 2, 2007, pp. 1767-1771.
Li-Li Ma et al., "Preparation, characterization and photocatalytic properties of CdS nanoparticles dotted on the surface of carbon nanotubes", Nanotechnology, vol. 19, No. 11, dated Feb. 19, 2008, p. 115709.

* cited by examiner

FIG. 17(A)
FIG. 17(B)
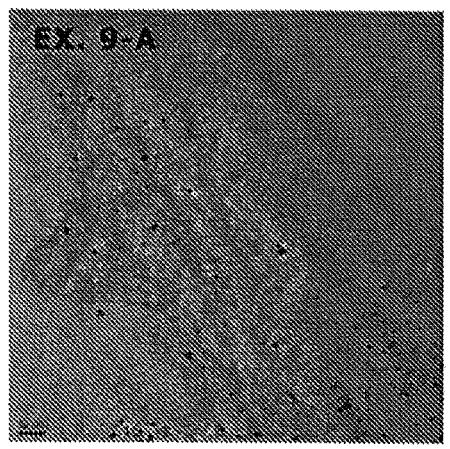
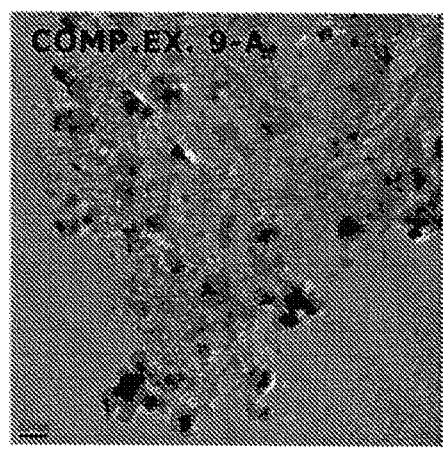
FIG. 18
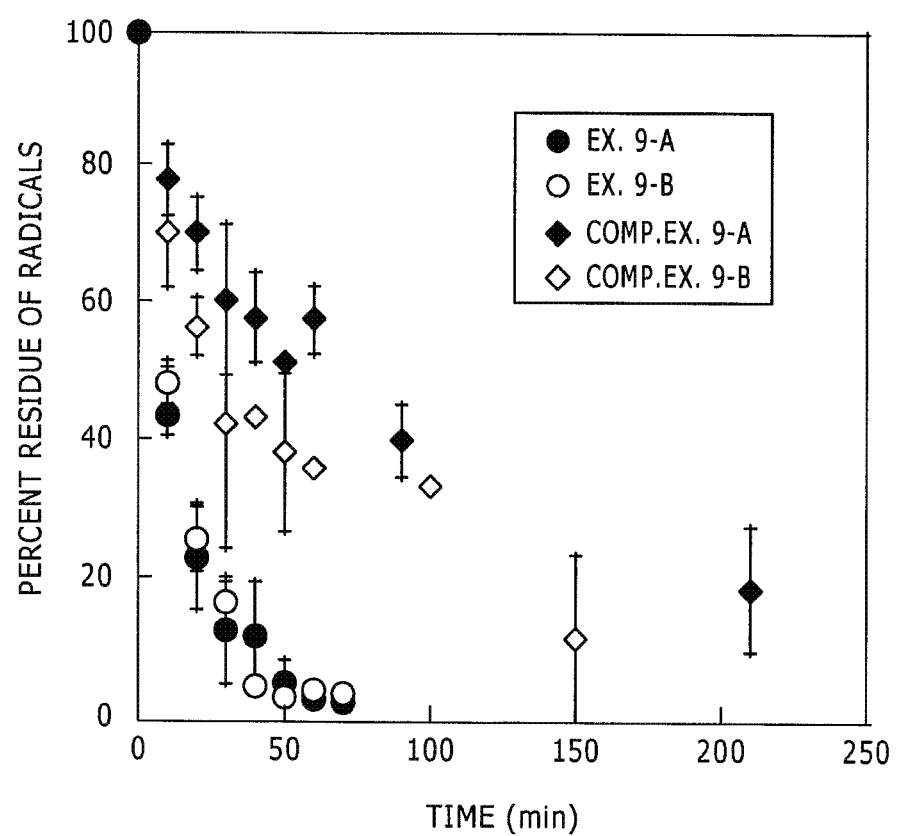

POROUS CARBON MATERIAL COMPOSITES AND THEIR PRODUCTION PROCESS, ADSORBENTS, COSMETICS, PURIFICATION AGENTS, AND COMPOSITE PHOTOCATALYST MATERIALS

RELATED APPLICATION DATA

This application is a divisional of U.S. patent application Ser. No. 15/876,382 filed Jan. 22, 2018, which is a continuation of U.S. Ser. No. 15/140,569 filed Apr. 28, 2016 now abandoned, which is a division of U.S. patent application Ser. No. 12/741,967 filed May 7, 2010 now abandoned. U.S. patent application Ser. No. 12/741,967 is the Section 371 National Stage of PCT/JP2009/066737 filed Sep. 28, 2009. These applications are all incorporated herein by reference to the extent permitted by law. The present application claims the benefit of priority to Japanese Patent Application No. JP 2008-250679 filed on Sep. 29, 2008 and Japanese Patent Application No. JP 2009-184350 filed on Aug. 7, 2009 in the Japan Patent Office, the entireties of which are incorporated by reference herein to the extent permitted by law.

TECHNICAL FIELD

This invention relates to porous carbon material composites making use of plant-derived materials as raw materials and their production process, and also to adsorbents, cosmetics, purification agents and composite photocatalyst materials, all of which are composed of the porous carbon material composites.

BACKGROUND ART

Functional materials which are each obtainable by imparting a physical or physicochemical property such as, for example, a magnetic property, a light absorption property, a light emission property, or adsorption ability for a specific substance to porous materials are materials of high interest, because they each have both a large specific surface area and the physical property imparted to the functional material. These porous materials can include alumina, carbon, silica, and the like. Functional materials, each of which has a magnetic property, a property that shows a unique behavior to light (such a property will hereinafter be called "an optical property" for the sake of convenience) or a property having adsorbing ability for a specific substance, can include fine particles or thin films of metals (Fe, Co, Ni, Au, Ag, Pt, Cu) and alloys, oxides ($Fe_2O_3$, $Fe_3O_4$, $TiO_2$, $ZnO_2$), compounds (CdS, CdSe, ZnS, $CaCO_3$, $Ca(CH_3COO)_2$), or the like, and high molecular films and monomolecular films containing many amino groups.

Such functional materials are expected to find applications, for example, in adsorbents, catalysts, electrodes for energy devices, and sensing devices (see, for example, Japanese Patent Laid-open No. 2006-167694). Unused parts of plants such as vegetables and grain crops are mostly discarded, but effective utilization of these unused parts is strongly desired for the reservation and improvement of the global environment. As one example of such effective utilization of unused parts, carbonization treatment can be mentioned. One example of the use of a carbon material, which has been produced by subjecting such a plant-derived material to carbonization treatment, as a colorant adsorbent is known, for example, from Dyes and Pigments, 66, 123 to 128 (2005). Further, a process for producing a char having deodorant ability, ion-exchange ability or catalytic ability from a plant material is known well from Japanese Patent Laid-open No. 2000-211910.

In an eutrophic lake, marsh or pond, a blue-green alga (Microcystis aeruginosa or the like) may abnormally proliferates around the summer time, so that a thick layer may be formed as if the water surface is dusted with a green powder. This thick layer is called "water bloom." Such blue-green algae are known to release toxins harmful to human bodies, and among many toxins, a toxin called "microcystin LR" requires special vigilance. An introduction of microcystin LR into the body inflicts significant damage on the liver, and its toxicity has also been reported based on experiments on mice. Toxic water blooms that release microcystin LR are growing in Australian, European and American lakes and various Asian areas. In seriously-inflicted Chinese lakes, explosively grown water blooms do not disappear all the year round. Since lake water is used as drinking water or agricultural water, the toxins released by blue-green algae in lakes and marshes are at issue for the securement of human drinking water, leading to an outstanding strong desire for its resolution.

Zeolite and activated carbon are porous materials having very fine pore structures of several nanometers and are used in various fields. Their functions widely range, including separation, removal, storage, catalyzing and so on. In recent years, they are also expected to find utility as drug carriers in drug delivery systems (DDS).

Superoxides, hydroxy radicals, hydrogen peroxide and singlet oxygen are know to be reactive oxygen species in broad sense, and are considered to be causes of acute inflammatory, tissue damage and aging. Antioxidant ingredients, which have been conventionally used to cope with these oxidizing substances, can include vitamin C (L-ascorbic acid), astaxanthin, coenzyme Q10, and the like. However, L-ascorbic acid salts, L-ascorbic acid derivatives and the like have a problem with stability so that they themselves are oxidized as a result of single reducing action. As a solution for this problem, cosmetics containing platinum nanocolloid have been proposed in recent years. These cosmetics are each intended to activate the horny layer of skin by applying electric double layers, which the highly active platinum colloid has, to the skin and protecting it (see, for example, Japanese Patent Laid-open No. 2005-139102). Nanosize platinum particles have merits such that they retain antioxidation ability and high catalytic ability over long term, have high reactivity at their surfaces and can eliminate various reactive oxygen species, so that they are incorporated in many cosmetics.

Numerous beauty ingredients are contained in cosmetic waters and packs soaked with cosmetic water, which are currently available on the market. Many of these beauty ingredients are hydrophobic molecules, and therefore, are often insoluble or sparingly soluble in water. A number of solubilizers are, therefore, used to solubilize these beauty ingredients, and in particular, solubilizers excellent in stability are widely used. Employed as solubilizers are non-ionic surfactants containing polyoxyethylene chains, such as polyoxyethylene oleyl ether, polyoxyethylene sorbitan oleate and polyoxyethylene hydrogenated castor oil; and anionic surfactants such as sodium lauryl sulfate, sodium dodecylbenzenesulfonate and potassium myristate.

CITATION LIST

Patent Literature

PTL 1: Japanese Patent Laid-open No. 2006-167694
PTL 2: Japanese Patent Laid-open No. 2000-211910
PTL 3: Japanese Patent Laid-open No. 2005-139102

Non-Patent Literature

NPL 1: Dyes and Pigments, 66, 123-128 (2005)

SUMMARY OF INVENTION

Technical Problem

As described above, there have been reported functional materials with functional materials, which are formed of inorganic materials, combined with porous carbon materials that make use of plant-derived materials as raw materials. However, technologies for subjecting such plant-derived materials to carbonization treatment are not considered to be sufficient. There is, accordingly, an outstanding desire for further improvements in the properties and functionality of functional materials (porous carbon material composites) based on porous carbon materials.

In the removal of a toxin released by a blue-green alga and having a molecular weight of 500 or higher, the use of a conventional adsorption method that makes use of activated carbon results in a very small amount of its adsorption per unit weight because the pore size of the activated carbon is very small. A still further improvement in functionality is, therefore, desired in the method that removes a toxin by using a carbon material. As a requirement for practical applications, on the other hand, it can be mentioned that:

[A] the removal method can be practiced as a system that can surely detoxify microcystins, that is, toxic components dissolved out upon disposal of water blooms, and further, it is desired inter alia that:

[B] the removal method does not cause secondary pollution of the environment by a material or the like employed, and

[C] the treatment system is economical and is easy to handle, can be recovered as needed, and does not disturb the environmental ecosystem.

For a drug delivery system (DDS), it is very important to administer a drug to a necessary site or region in a necessary amount. With current porous materials, however, it is impossible to control desorption although they are excellent in adsorption properties. Mechanisms, features and/or structures, which make it possible to control the release of carried substances based on various external stimuli such as temperature and humidity, are also required in various technical fields and industrial fields in addition to drug delivery systems.

The above-mentioned cosmetics with platinum nanocolloid contained therein need to use a protective colloid agent for forming nanosize fine particles of platinum into a colloid. However, the particles are covered as surfaces thereof with the protective colloid agent, so that their effect may not be expected in some instances. A still higher antioxidation effect can hence be expected if the fine particles can be maintained in nanosize without using a surface protective agent.

The above-mentioned surfactants employed in cosmetic waters and packs soaked with cosmetic water are not fully satisfactory in safety. Methods have also come under study in recent years to use high-molecular compounds which are considered to be higher in safety than the conventional surfactants. The use of these high-molecular compounds are, however, accompanied by problems such that the solubilization step is complex and the production cost is high.

Objects of the present invention are, therefore, to provide a porous carbon material composite, which is formed of a porous carbon material and a functional material and can be equipped with high functionality, and its production process, and an adsorbent, cosmetic, purification agent and composite photocatalyst material, all of which are composed of the porous carbon material composite.

Solution to Problem

A porous carbon material composite according to the present invention for achieving the above-described corresponding object includes:

(A) a porous carbon material obtainable from a plant-derived material having a silicon (Si) content of 5 wt % or higher as a raw material, said porous carbon material having a silicon (Si) content of 1 wt % or lower, and (B) a functional material adhered on the porous carbon material, wherein the porous carbon material composite has a specific surface area of 10 $m^2/g$ or greater as determined by the nitrogen BET method and a pore volume of 0.1 $cm^3/g$ or greater as determined by the BJH method and MP method.

A process according to the present invention for producing a porous carbon material composite and achieving the above-described corresponding object includes the following steps: carbonizing a plant-derived material at from 800° C. to 1,400° C., treating the carbonized material with an acid or alkali to obtain a porous carbon material, and then causing a functional material to adhere on the porous carbon material.

An adsorbent according to the present invention for achieving the above-described corresponding object includes:

(A) a porous carbon material obtainable from a plant-derived material having a silicon content of 5 wt % or higher as a raw material, said porous carbon material having a silicon content of 1 wt % or lower, and (B) a magnetic material adhered on the porous carbon material, wherein the adsorbent has a specific surface area of 10 $m^2/g$ or greater as determined by the nitrogen BET method and a pore volume of 0.1 $cm^3/g$ or greater as determined by the BJH method and MP method, and wherein the adsorbent can adsorb a microcystin thereon.

A composite photocatalyst material according to the present invention for achieving the above-described corresponding object includes a porous carbon material composite, wherein the porous carbon material composite includes:

(A) a porous carbon material obtainable from a plant-derived material having a silicon content of 5 wt % or higher as a raw material, said porous carbon material having a silicon content of 1 wt % or lower, and (B) a photocatalyst material adhered on the porous carbon material, wherein the porous carbon material composite has a specific surface area of 10 $m^2/g$ or greater as determined by the nitrogen BET method and a pore volume of 0.1 $cm^3/g$ or greater as determined by the BJH method and MP method.

A cosmetic according to the present invention for achieving the above-described corresponding object includes a porous carbon material composite, wherein the porous carbon material composite includes:

(A) a porous carbon material obtainable from a plant-derived material having a silicon content of 5 wt % or higher as a raw material, said porous carbon material having a silicon content of 1 wt % or lower, and (B) a metal-based material adhered on the porous carbon material and having a reactive oxygen removing effect, wherein the porous carbon material composite has a specific surface area of 10 m²/g or greater as determined by the nitrogen BET method and a pore volume of 0.1 cm³/g or greater as determined by the BJH method and MP method.

A purification agent according to the present invention for achieving the above-described corresponding object includes a porous carbon material composite, wherein the porous carbon material composite includes:

(A) a porous carbon material obtainable from a plant-derived material having a silicon content of 5 wt % or higher as a raw material, said porous carbon material having a silicon content of 1 wt % or lower, and (B) a photocatalyst material adhered on the porous carbon material, wherein the porous carbon material composite has a specific surface area of 10 m²/g or greater as determined by the nitrogen BET method and a pore volume of 0.1 cm³/g or greater as determined by the BJH method and MP method.

Advantageous Effects of Invention

Concerning the porous carbon material composite according to the present invention or the porous carbon material composite obtainable by the production process according to the present invention, or the adsorbent, cosmetics, purification agent or composite photocatalyst material according to the present invention, silicon is contained at 5 wt % or more in the plant-derived material. However, by carbonizing the plant-derived material at from 800° C. to 1,400° C. upon its conversion into a porous carbon material precursor [1] or carbonaceous material [1] to be described subsequently herein, the silicon contained in the plant-derived material is not converted into silicon carbide (SiC) but is converted into silicon components (oxidized silicon compounds) such as silicon dioxide ($SiO_x$), silicon oxide and silicon oxide salts. By conducting treatment with an acid or alkali (base) in the subsequent step, the silicon components (oxidized silicon compounds) such as silicon dioxide, silicon oxide and silicon oxide salts are thus eliminated. As a result, it is possible to obtain a large value of specific surface area as determined by the nitrogen BET method. Described specifically, it is possible to obtain a porous carbon material having a specific surface area value of 10 m²/g or greater as determined by the nitrogen BET method, a silicon content of 1 wt % or lower, and a pore volume of 0.1 cm³/g or greater as determined by the BJH method and MP method. By causing a functional material to adhere on such a porous carbon material, the functional material can be caused to adhere in an increased amount per unit gram of porous carbon material, thereby making it possible to obtain a porous carbon material composite having high properties and high functionality.

When a magnetic material is caused to adhere on such a porous carbon material, the magnetic material is allowed to adhere in an increased amount per unit weight of porous carbon material, thereby making it possible to obtain an adsorbent having excellent properties and high functionality, for example, an adsorbent which can be easily separated from water by magnetic separation equipment. As a consequence, microcystins contained as toxic components in water blooms, lake or marsh water, river water or the like can be adsorbed easily, surely and economically, and moreover, without causing secondary pollution of the environment and disturbing the environmental biosystem.

As mentioned above, the porous carbon material in the present invention is an environment compatible material derived from a natural product, and its microstructure can be obtained by treating and removing silicon components (oxidized silicon compounds), which are inherently contained in a plant-derived material as a raw material, with an acid or alkali. Therefore, its pores have sizes unrealizable with conventional activated carbon or sizes in a meso range (2 to 50 nm), and the array of pores still retains the bioregularity of the plant. In the composite photocatalyst material according to the present invention, the photocatalyst material is caused to adhere on the porous carbon material extremely effectively owing to such a pore size and array, thereby making it possible to effectively induce decomposition by a photocatalytic effect. In the cosmetic according to the present invention, the metal-based material having a reactive-oxygen removing effect is carried extremely effectively on the porous carbon material owing to such a pore size and array. It is, therefore, no longer essential to use a protective colloid agent, for example, for forming fine platinum particles of nanosize into a colloid, thereby making it possible to exhibit a high antioxidation effect against reactive oxygen species such as superoxides, hydroxy radicals, hydrogen peroxide and singlet oxygen which are considered to be causes of acute inflammatory, tissue damage and aging. In the purification agent according to the present invention, that is, an environment purification material, such a pore size and array is also considered to effectively act for the adsorption of a toxic substance, and at the same time, can cause the photocatalyst material to adhere on the porous carbon material extremely effectively, thereby effectively inducing the decomposition and detoxification of a toxic substance by a photocatalytic effect. Moreover, the spreading of the toxic substance inside the purification agent can be promoted, thereby making it possible to more effectively induce the decomposition by the photocatalytic effect and to conduct the purification of water or the purification of air extremely effectively.

BRIEF DESCRIPTION OF DRAWINGS

FIGS. 17(A) and 17(B) are electron micrographs of Example 9-A and Comparative Example 9-A.

FIG. 18 is a graph showing changes with time in the percent residues of radicals in Example 9-A, Example 9-B, Comparative Example 9-A and Comparative Example 9-B.

MODES FOR CARRYING OUT THE INVENTION

Figure 1A:
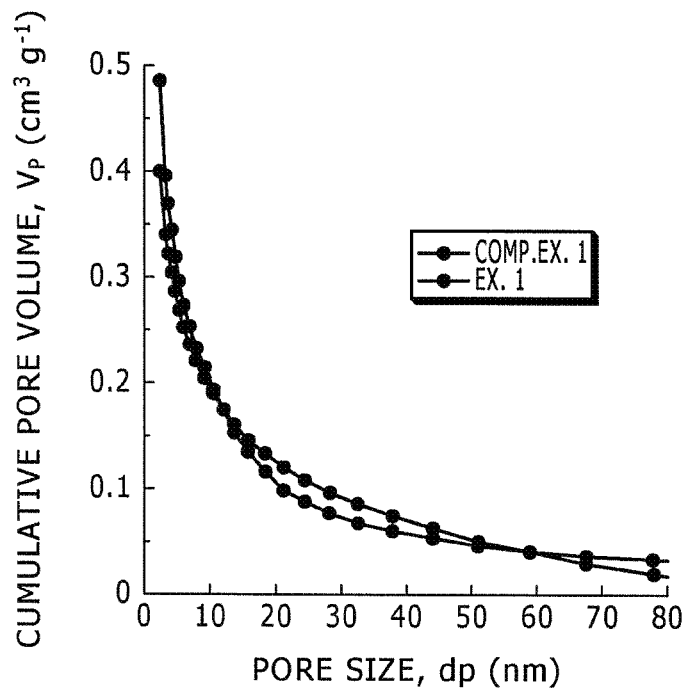
FIGS. 1(A) and 1(B) are graphs showing the pore size distributions of mesopores and the pore size distributions of micropores in a porous carbon material composite of Example 1 and a porous carbon material of Comparative Example 1, respectively.

With reference to the drawings, the present invention will hereinafter be described based on examples. It should, however, be borne in mind that the present invention is not limited to the examples and that various data and materials in the examples are illustrative. The description will be made in the following order.
1. General description on the porous carbon material composite and its production process and the adsorbent, all according to the present invention.
2. Example 1 (a porous carbon material composite and its production process, both of the present invention)
3. Example 2 (a modification of Example 1)
4. Example 3 (another modification of Example 1)
5. Example 4 (a modification of Example 3)
6. Example 5 (a further modification of Example 1)
7. Example 6 (a modification of Example 5)
8. Example 7 (a still further modification of Example 1, a composite photocatalyst material and purification agent, both of the present invention)
9. Example 8 (an adsorbent of the present invention)
10. Example 9 (an even still further embodiment of Example 1, etc.)
11. Example 10 (yet even a still further embodiment of Example 1, etc.)
[General Description on the Porous Carbon Material Composite and its Production Process and the Adsorbent, Cosmetic, Purification Agent and Composite Photocatalyst Material, all According to the Present Invention]

The porous carbon material composite according to the present invention can be obtained not only by the above-described production process according to the present invention for porous carbon material composite but also by a production process that includes subjecting the plant-derived material to heat treatment (precarbonization treatment) at a temperature (for example, from 400° C. to 700° C.) lower than a temperature for carbonization to be conducted in a subsequent step and under oxygen-free conditions, treating the heat-treated material with an acid or alkali, conducting the carbonization at from 800° C. to 1,400° C. to obtain a porous carbon material, and then causing a functional material to adhere on the porous carbon material. It is to be noted that such a production process may be called "the second production process" for the sake of convenience, and further, that the production process according to the present invention for the porous carbon material composite may be called "the first production process" for the sake of convenience.

In the first production process, it is possible to further include a step that applies activation treatment after the treatment with the acid or alkali but before the adhesion of the functional material on the porous carbon material. In the first production process including such a preferred embodiment, heat treatment (precarbonization treatment) may be applied, depending on the plant-derived material to be used, to the plant-derived material at a temperature (for example, from 400° C. to 700° C.) lower than the temperature for carbonization and under oxygen-free conditions before the carbonization of the plant-derived material. By this heat treatment, or in the second production process, as a result that tar components which would otherwise be formed in the course of the carbonization can be extracted, the tar components which would be formed in the course of carbonization can be decreased or eliminated. It is to be noted that the oxygen-free conditions can be achieved, for example, by employing an atmosphere of inert gas such as nitrogen gas or argon gas or a vacuum atmosphere or by forming the plant-derived material into a sort of steamed and baked state. In the first production process or second production process, the plant-derived material may be immersed, depending on the plant-derived material to be used, in an alcohol (for example, methyl alcohol, ethyl alcohol or isopropyl alcohol) to decrease mineral components and water contained in the plant-derived material and also to prevent the production of an offensive odor in the course of carbonization. It is to be noted that in the first production process, precarbonization treatment may be conducted subsequently. As materials to which heat treatment may preferably be applied in an inert gas, plants that abundantly produce pyroligneous acid (tar components and light oil fractions) can be mentioned, for example. As materials to which the alcohol pretreatment may preferably be applied, marine algae that abundantly contain iodine and various minerals can be mentioned, for example. In the second production process, a step that applies activation treatment may be included after the carbonization but before causing the functional material to adhere on the porous carbon material.

The first production process or second production process, including the above-described, various preferred embodiments, can be embodied such that content of silicon (Si) in the plant-derived material is 5 wt % or higher, the content of silicon (Si) in the porous carbon material is 1 wt % or lower, the value of specific surface area of the porous carbon material composite as determined by the nitrogen BET method is 10 $m^2/g$ or greater, and the pore volume of the porous carbon material composite as determined by the BJH method and MP method is 0.1 $cm^3/g$ or greater.

The porous carbon material composite and its production process according to the present invention, including the above-described various preferred embodiments and features, the adsorbent according to the present invention, the cosmetic according to the present invention, the purification agent according to the present invention, and the composite photocatalyst material according to the present invention may be collectively called simply "the present invention." The porous carbon material composite according to the present invention and the porous carbon material composite produced by the production process according to the present invention or the second production process, including the above-described various preferred embodiments and features, may be collectively called simply "the porous carbon material composite or the like according to the present invention." The porous carbon material composite according to the present invention and the porous carbon material composite produced by the production process according to the present invention or the second production process, including the above-described various preferred embodiments and features, and the adsorbent according to the present invention, the cosmetic according to the present invention, the purification agent according to the present invention and the composite photocatalyst material according to the present invention may be collectively called simply "the porous carbon material composite or the like according to the present invention." The material obtained by carbonizing the plant-derived material at from 800° C. to 1,400° C. but not subjected yet to the treatment with the acid or alkali in the first production process will be called "the porous carbon material precursor [1]" or "the carbonaceous material [1]." Further, the material after the precarbonization treatment but before the treatment with the acid or alkali in the second production process will be called "the porous carbon material precursor [2]."

In the porous carbon material composite according to the present invention, the functional material can be a magnetic material. In this case, or in the case of the adsorbent according to the present invention, the magnetic material may desirably contain, as a constituent element, at least one element selected from the group consisting of iron (Fe), cobalt (Co) and nickel (Ni). Further, the magnetic material may desirably be contained at 1 wt % or higher, preferably at 10 wt % or higher in a state that it exhibits magnetism in the porous carbon material composite or the like according to the present invention. The value of upper limit of the magnetic material contained in the porous carbon material can be determined based on properties required for the porous carbon material composite or the like according to the present invention. Described specifically, the value of saturation mass magnetization of the porous carbon material composite or the like according to the present invention may desirably be 1 $A·m^2/kg$ or higher, with 10 $A·m^2/kg$ or higher being preferred. Further, as the value of upper limit of saturation mass magnetization of the porous carbon material composite or the like according to the present invention, 150 $A·m^2/kg$ can be mentioned as an illustrative example. More specific examples of the magnetic material can include ferromagnetic materials such as nickel (Ni), iron (Fe) and cobalt (Co), alloys of these ferromagnetic materials (for example, Co—Fe, Co—Fe—Ni, Ni—Fe and the like), alloys (for example, Co—Fe—B and the like) obtained by mixing nonmagnetic elements (for example, tantalum, boron, chromium, platinum, silicon, carbon, nitrogen, phosphorus and the like) in the above-described alloys, oxides (for example, ferrite, Fe—MnO and the like) containing one or more of Co, Fe and Ni, a group of intermetallic compounds called "half-metallic ferromagnetic materials" (Heusler alloys: $NiMnSb$, $Co_2MnGe$, $Co_2MnSi$, $Co_2CrAl$ and the like), and oxides (for example, $(La, Sr)MnO_3$, $CrO_2$, $Fe_3O_4$ and the like). When such a magnetic material is used as the functional material, an adhesion in the form of fine particles or an adhesion in the form of thin films can be exemplified as the state of adhesion of the functional material on the porous carbon material. The porous carbon material composite according to the present invention has been imparted with magnetism, and therefore, can be used in applications such as magnetically-inducible adsorbents, sustained release agents, cell culture scaffolds (surface property control by an a.c. magnetic field or a temperature-responsive polymer), blood flow stimulators making use of produced magnetic fields, water purification, and soil purification.

As an alternative, the functional material in the porous carbon material composite according to the present invention can be embodied such that it exhibits an optical property. The term "optical property" as used herein means "surface plasmon absorption" or "light absorption by a semiconductor." As another alternative, the functional material can be embodied such that it is formed of a noble metal, including platinum (Pt), palladium (Pd), gold (Au), silver (Ag) or copper (Cu); an alloy of a noble metal; an oxide semiconductor such as titanium oxide or zinc oxide; or a compound semiconductor such as cadmium sulfide, lead sulfide, cadmium selenide, lead selenide, zinc selenide, indium arsenide, gallium arsenide, indium phosphide, gallium phosphide, gallium antimonide, indium antimonide, titanium oxide or lanthanide oxide. Selection of the functional material from noble metals or its alloys makes it possible to exhibit an optical property called "surface plasmon absorption," thereby enabling applications in sensors that detect reactions in changes in surface plasmon absorption (color tone) and also in cell culture scaffolds (effects of plasmon resonance on cells). Selection of the functional material from oxide semiconductors or compound semiconductors makes it possible to exhibit an optical property such as an absorption of light or an emission of light by the semiconductor. Formation of the functional material with a noble metal, including platinum (Pt), palladium (Pd), gold (Au), silver (Ag) or copper (Cu), or an alloy of such a noble metal makes it possible to provide the porous carbon material composite with a high antioxidation effect against reactive oxygen species. As the states of adhesion of these functional materials on the porous carbon material, an adhesion in the form of fine particles and an adhesion in the form of thin films can be mentioned as illustrative examples.

As a further alternative, the functional material in the porous carbon material composite according to the present invention can be embodied such that it exhibits a photocatalytic property. When the functional material is formed of platinum (Pt), platinum (Pt) or palladium (Pd), an adhesion in the form of fine particles or an adhesion in the form of thin films can be mentioned as an illustrative state of adhesion of the functional material on the porous carbon material. A catalytic property is hence imparted to the porous carbon material composite, thereby enabling an application as an electrode material and also enabling applications for the removal of $NO_x$ and $SO_x$ in exhaust gases from internal combustion engines in automotive vehicles, combustion apparatuses, engines and the like. When the functional material is formed of titanium oxide ($TiO_2$) or zinc oxide (ZnO), an adhesion in the form of fine particles or an adhesion in the form of thin films can be mentioned as an illustrative state of adhesion of the functional material on the porous carbon material. A charge separation, ultraviolet absorption or catalytic property is hence imparted to the porous carbon material composite, so that owing to a photocatalyst effect, applications are feasible as toxic substance decomposing agents or toxic substance removing agents that are usable semi-permanently.

It is to be noted that the formation of a photocatalyst material (functional material) with titanium oxide or zinc oxide makes it possible to obtain a composite photocatalyst material according to the present invention or a purification agent according to the present invention. For the decomposition and removal of toxic substances, it is possible to mention an embodiment that exposes the porous carbon material composite according to the present invention to energy radiation or electromagnetic waves (for example, ultraviolet rays, sunlight, visible light, or the like). The toxic substances include toxic substances that exist in water or air. Specifically, microcystins, various viruses and allergy causative substances can be mentioned as illustrative examples. The purification agent according to the present invention functions as a water purifying agent or air purifying agent, and can be applied, for example, as filters for air purification apparatuses. As application forms of the composite photocatalyst material and purification agent according to the present invention, their applications in the forms of sheets, their applications in the forms that they are packed in columns or cartridges, their applications in the forms of desired shapes formed by binders or the like, and their applications in powdery forms can be mentioned as illustrative examples.

As a still further alternative, the functional material in the porous carbon material composite according to the present invention can be formed of an external stimulus responsive substance and a releasable substance. Described specifically, it is possible to control a change in the structure of the external stimulus responsive substance by an external stimulus, and further, to control the desorption of the releasable substance, which is adhered, bound, adsorbed or carried on the porous carbon material (in some instances, also the external stimulus responsive substance), from the porous carbon material. The formation of the functional material with the external stimulus responsive substance makes it possible, for example, to administer a drug to a necessary site in a needed amount only. An external stimulus responsive substance made of a high-molecular material or oligomer changes in structure upon receipt of a stimulus from the outside. The porous carbon material in the present invention has pores of sizes unrealizable with conventional activated carbon or sizes in a meso range (2 to 50 nm), can sufficiently reflect a change that takes place when the external stimulus responsive substance responds to an external stimulus, and based on this change, can release the releasable substance. Conventional porous materials such as activated carbon and zeolite, on the other hand, are so small in pore size that they cannot sufficiently reflect a change that takes place when the external stimulus responsive substance responds to an external stimulus. When light is assumed as a physical external stimulus, azobenzene, coumarin, and naphthoquinone diazide compounds can be mentioned as external stimulus responsive substance, that is, light responsive substances. When a temperature is assumed as a physical external stimulus, external stimulus responsive substances, that is, temperature responsive substances include poly-N-isopropyl acrylamide (IPAAm), polyethylene oxide (for example, polyethylene oxide having a molecular weight of from 1,000 to 2,000, PEO 1,000 to 2,000), and gelatin. When a humidity is assumed as a physical external stimulus, external stimulus responsive substances, that is, humidity responsive substances include polyethylene glycol and hyaluronic acid. When a pH is assumed as a chemical external stimulus, external stimulus responsive substances, that is, pH responsive substances include polymers containing acid-dissociable functional groups such as carboxyl groups and/or amino groups. When an ionic strength is assumed as a chemical external stimulus, polymers containing functional groups ion-exchangeable with metal ions, such as carboxyl groups and/or amino groups, can be mentioned as external stimulus responsive substances, that is, ionic-strength responsive substances.

As releasable substances, drugs to be carried on DDS carriers, transdermal drugs, cell culture scaffolds, cosmetic ingredients, ingredients having a moisturizing effect and/or an antioxidation effect, and fragrances can be mentioned as illustrative examples. More specifically, drugs to be carried on DDS carriers can include morphine, anticancer agents and the like. Transdermal drugs can include nitroglycerin and isosorbide dinitrate for angina, and tulobuterol as an asthma drug, and a smoking-cessation nicotine patch. Cell culture scaffolds can include nutrients for cells, such as casein and glucose. Cosmetic ingredients can include substances having hydrophobic beauty ingredients (for example, daidzein and genistein). Ingredients having a moisturizing effect and/or antioxidation effect can include effective ingredients contained in cosmetic waters, such as hyaluronic acid, astaxanthin, tocopherol, Trolox, and coenzyme Q10. Further, fragrances can include limonene, menthol, linalool, vanillin, and the like. A porous carbon material composite can be obtained, for example, by formulating such a releasable substance into a liquid, immersing a porous carbon material in the liquid, drying the immersed porous carbon material, formulating such an external stimulus responsive substance into a liquid, immersing the porous carbon material with the releasable substance adhered, bound, adsorbed or otherwise carried thereon, and then drying the immersed porous carbon material, although its production process is not limited to such a process.

Transdermal absorption is useful as an administration method that causes relatively less side effects, but the persistence of current transdermal drugs is not considered to be fully sufficient. A porous carbon material composite is available by modifying a porous carbon material with a polymer (temperature responsive substance or body-temperature responsive substance) that undergoes a structural change around the body temperature. This porous carbon material composite is extremely useful as a carrier for a transdermal drug. The transdermal drug has an excellent characteristic that from a portion warmed by the body temperature, a releasable substance, that is, a transdermal drug ingredient is gradually released, and hence, is provided with an improved sustained-release property.

In a wide variety of cosmetics currently available on the market such as cosmetic waters and packs impregnated with cosmetic water, many beauty ingredients are contained. However, many of these beauty ingredients are hydrophobic molecules, and are often insoluble or sparingly insoluble in water. In the present invention, a releasable substance adheres on a porous carbon material, and different from the conventional technologies, requires neither a surfactant nor a high-molecular compound. Moreover, a porous carbon material composite is available by modifying the porous carbon material with a polymer (a temperature responsive substance or humidity responsive substance) which undergoes a structural change around the body temperature such that the carried releasable substance (a cosmetic ingredient or an ingredient having a moisturizing effect and/or an antioxidation effect) can be released upon use of the cosmetic. This porous carbon material composite is extremely preferred as a material for carrying the releasable substance, that is, the cosmetic ingredient or the ingredient having the moisturizing effect and/or the antioxidation effect. In addition, the porous carbon material composite also has a cleansing effect, and therefore, can also remove stain components such as sweat, sebum and a lipstick. The term "stain components" specifically indicates, for example, oil, fat and sebum composed of fatty acid glycerin esters, lipids such as simple lipids, complex lipids and derived lipids, and organic acids as components of wax and the like; especially all oils found on the human skin surface (fatty acids in a broad sense); and also includes, in a narrow sense, fatty acids containing linear or branched chains or cyclic structures, such as saturated fatty acids and unsaturated fatty acids. The fatty acids specifically include oleic acid, stearic acid, myristic acid, squalene (an oil belonging to terpenoids), cholesterol (biosynthesized from squalene), and monoglyceryl stearate. Pigments contained in lipsticks can specifically include all officially-approved pigments (tar pigments) including Lithol Rubin BCA (Pigment Red 57:1).

The porous carbon material is useful as a scaffold material for culturing cells. It is extremely important that a releasable substance, that is, an ingredient important for culturing is gradually released from the scaffold material heated to around 37° C., that is, a culturing temperature. A porous carbon material composite obtainable by modifying a porous carbon material with a polymer (a temperature responsive substance), which undergoes a structural change around the body temperature, is extremely preferred as a cell culture scaffold material.

Many fragrances having high sustainability are commercially available these days, but do not include such a fragrance that responds to an external stimulus. A porous carbon material composite, which is available by modifying a porous carbon material with a polymer that undergoes a structural change by a temperature or humidity, can release, for example, a fragrance (releasable substance) having such an effect as relaxing one's mood under an environment of such a temperature or humidity as making him or her feel unpleasant.

As an even still further alternative, the functional material in the porous carbon material composite according to the present invention can also be composed of an ingredient having a moisturizing effect and/or an antioxidation effect (or a beauty ingredient). Examples of the ingredient having the moisturizing effect and/or the antioxidation effect can include hyaluronic acid, astaxanthin, tocopherol, Trolox, coenzyme Q10, and collagen. They are conventionally contained, for example, in cosmetic waters. It is to be noted that such a porous carbon material composite also has a cleansing effect and can remove stain components such as sweat, oil, fat and a lipstick.

In the cosmetic according to the present invention, platinum nanoparticles can be mentioned as an example of the metal-based material having a reactive oxygen removing effect (a metal-based material capable of removing reactive oxygen). It is to be noted that the cosmetic according to the present invention also has a cleansing effect and can remove stain components such as sweat, oil, fat and a lipstick.

As yet even a still further alternative, the functional material in the porous carbon material composite according to the present invention can be embodied such that it exhibits a selective adsorbing or binding property to a specific substance. In this alternative, the functional material can be embodied such that it is composed of a compound that binds to phosphorus to precipitate (for example, calcium carbonate or calcium acetate), a molecule film having phosphorus-adsorbing sites (for example, a high-molecular film having amino groups—specifically, for example, sevelamer hydrochloride), a monomolecular film having amino groups (specifically, for example, 3-aminopropyltriethoxysilane).

In each porous carbon material composite or the like according to the present invention, including the above-described various preferred embodiments and features, grain husks or straws of rice (rice plant), barley, wheat, rye, barnyardgrass or foxtail millet, reed, or seaweed stems can be mentioned as the plant-derived material. However, the plant-derived material is not limited to such materials, and in addition to them, vascular plants, ferns and mosses which grow on land, algae, and seaweeds can also be mentioned, for example. It is to be noted that as a raw material, these materials may be used singly or plural ones of them may be used in combination. Further, no particular limitation is imposed on the shape or form of the plant-derived material. For example, grain husks or straws may be used as they are, or may be used in the form of a dried product. It is also possible to use one subjected to one or more of various treatments such as fermentation processing, roasting processing and extraction processing in the processing of a food or beverage such as beer or liquor. Especially from the viewpoint of achieving the recycling of an industrial waste as a resource, it is preferred to use straws or grain hulls after processing such as threshing. Straws or grain hulls after such processing can be obtained in a large volume and with ease, for example, from agricultural cooperative associations, alcoholic liquor manufacturers or food companies.

In each porous carbon material composite or the like according to the present invention, the state of adhesion of the functional material on the porous carbon material can be a state of adhesion as fine particles, a state of adhesion in the forms of thin films, or a state of adhesion in sea-island patterns (the functional material corresponds to "islands" when the surfaces of the porous carbon material are considered to be "seas"), on surfaces (including the interiors of pores) of the porous carbon material, although it depends on the kind, composition, structure or form of the functional material. It is to be noted that the term "adhesion" indicates adherence between dissimilar materials. As a method for causing the functional material to adhere on the porous carbon material, there can be mentioned a method that immerses the porous carbon material in a solution with the functional material contained therein and then causes the functional material to adhere on the surfaces of the porous carbon material, a method that causes the functional material to adhere on the surfaces of the porous carbon material by an electroless plating process (chemical plating process) or through a chemical reduction reaction, a method that immerses the porous carbon material in a solution with a precursor of the functional material contained therein and then conducts thermal treatment to cause the functional material to adhere on the surfaces of the porous carbon material, a method that immerses the porous carbon material in a solution with a precursor of the functional material contained therein and then conducts ultrasonic irradiation treatment to cause the functional material to adhere on the surfaces of the porous carbon material, or a method that immerses the porous carbon material in a solution with a precursor of the functional material contained therein and then conducts a sol-gel reaction to cause the functional material to adhere on the surfaces of the porous carbon material.

In the first production process or second production process, the plant-derived material is carbonized at from 800° C. to 1,400° C. The term "carbonized" as used herein means to subject an organic substance (the plant-derived material in the present invention) to heat treatment to convert it into a carbonaceous material (see, for example, JIS MO104-1984). As an atmosphere for carbonization, an oxygen-free atmosphere can be mentioned. Specifically, there can be mentioned a vacuum atmosphere, an inert gas atmosphere such as nitrogen gas or argon gas, or an atmosphere that forms the plant-derived material into a sort of steamed and baked state. As a ramp-up rate to a carbonization temperature, 1° C./min or higher, preferably 3° C./min or higher, more preferably 5° C./min or higher, each under such an atmosphere, can be mentioned. As an upper limit to the carbonization time, on the other hand, 10 hours, preferably seven hours, more preferably five hours can be mentioned, although the upper limit is not limited to such time. A lower limit to the carbonization time can be the time in which the plant-derived material can be surely carbonized. Further, the plant-derived material may be ground into a desired particle size as desired, and in addition, classification may be conducted. Furthermore, the plant-derived material may be washed beforehand.

When activation treatment is applied as mentioned above before causing the functional material to adhere on the porous carbon material subsequent to the treatment with the acid or alkali in the first production process or subsequent to the carbonization in the second production process, it is possible to increase micropores (to be described subsequently herein) the pore sizes of which are smaller than 2 nm. As an activation treatment method, a gas activation method or a chemical activation method can be mentioned. The term "gas activation method" as used herein means a method that oxygen, steam, carbon dioxide gas, air or the like is used as an activator and the porous carbon material is heated in such a gas atmosphere at 700° C. to 1,000° C. for several tens minutes to several hours to develop a microstructure by volatile components and carbon molecules in the porous carbon material. It is to be noted that the heating temperature may be chosen as desired based on the kind of the plant-derived material and the kind, concentration and the like of the gas. Preferably, however, the heating temperature may be 800° C. or higher but 950° C. or lower. The term "chemical activation method" as used herein, on the other hand, means a method that activation is effected using zinc chloride, iron chloride, calcium phosphate, calcium hydroxide, magnesium carbonate, potassium carbonate, sulfuric acid or the like in place of oxygen or steam employed in the gas activation method, washing is conducted with hydrochloric acid, the pH is adjusted with an aqueous alkaline solution, and drying is performed.

In the first production process or second production process, silicon components in the plant-derived material after its carbonization are removed by the treatment with the acid or alkali. Here, as the silicon components, oxidized silicon compounds such as silicon dioxide, silicon oxide and silicon oxide salts can be mentioned. By removing silicon components from the plant-derived material after its carbonization as described above, a porous carbon material having a high specific surface area can be obtained, thereby making it possible to increase the amount of the functional material to be caused to adhere per unit weight of the porous carbon material.

To the adsorbent according to the present invention, the porous carbon material composite according to the present invention, including the above-described embodiments and features, the porous carbon material composing the porous carbon material composite according to the present invention, and the first production process or second production process, including the above-described embodiments and features, can be applied.

In the porous carbon material or the like according to the present invention, nonmetal elements such as magnesium (Mg), potassium (K), calcium (Ca), phosphorus (P) and sulfur (S) and metal elements such as transition elements may be contained. The content of magnesium (Mg) can be 0.01 wt % or higher but 3 wt % or lower, the content of potassium (K) can be 0.01 wt % or higher but 3 wt % or lower, the content of calcium (Ca) can be 0.05 wt % or higher but 3 wt % or lower, the content of phosphorus (P) can be 0.01 wt % or higher but 3 wt % or lower, and the content of sulfur (S) can be 0.01 wt % or higher but 3 wt % or lower. It is to be noted that the lower the contents of these elements, the more preferred from the viewpoint of an increase in the value of specific surface area, although it differs depending on the application of the porous carbon material composite or the like according to the present invention. Needless to mention, the porous carbon material may also contain one or more elements other than the above-described elements, and the contents of such other elements may also vary depending on the application of the porous carbon material composite or the like according to the present invention.

In the present invention, the analyses of various elements can be performed by energy dispersion spectroscopy (EDS) while using, for example, an energy dispersive X-ray analyzer (for example, JED-2200F manufactured by JEOL Ltd.). As measurement conditions, the scanning voltage and irradiation current can be set, for example, at 15 kV and 10 µA, respectively.

The porous carbon material composite or the like according to the present invention has numerous pores. Contained as pores are "mesopores" the pore sizes of which range from 2 nm to 50 nm and "micropores" the pore sizes of which are smaller than 2 nm. Specifically, pores the pore sizes of which are, for example, 20 nm and smaller are contained numerously as mesopores, with pores the pore sizes of which are 10 nm and smaller being contained particularly numerously. As micropores, on the other hand, pores of 1.9 nm or so in pore size, pores of 1.5 nm or so in pore size and pores of from 0.8 nm to 1 nm or so in pore size are contained numerously. In the porous carbon material composite or the like according to the present invention, the pore volume as measured by BJH method and MP method is 0.1 cm$^3$/g or greater, with 0.3 cm$^3$/g or greater being still more preferred.

In the porous carbon material composite or the like according to the present invention, it is desired that the value of specific surface area as measured by the nitrogen BET method (which may hereinafter be called simply "the value of specific surface area") may be preferably 50 m$^2$/g or greater, more preferably 100 m$^2$/g or greater, still more preferably 400 m$^2$/g or greater to obtain still better functionality.

The term "the nitrogen BET method" means a method that measures an adsorption isotherm by adsorbing nitrogen as adsorbed molecules on an adsorbent (the porous carbon material composite in this context), desorbing it from the adsorbent, and analyzing measured data on the basis of a BET equation represented by the equation (1), and based on this method, a specific surface area, pore volume and the like can be calculated. Specifically, upon calculation of a value of specific surface area by the nitrogen BET method, an adsorption isotherm is first obtained by adsorbing nitrogen as adsorbed molecules on an adsorbent (the porous carbon material composite) and then desorbing it from the adsorbent. From the thus-obtained adsorption isotherm, $[p/\{V_a(p_0-p)\}]$ are calculated based on the equation (1) or an equation (1') derived by modifying the equation (1), and are plotted against the equilibrium relative pressure ($p/p_0$). Assuming these plots as a straight line, a slope $s (=[(C-1)/(C \cdot V_m)])$ and an intercept $i (=[1/(C \cdot V_m)])$ are then calculated based on the method of least squares. From the thus-determined slope $s$ and intercept $i$, $V_m$ and $C$ are calculated based on the equation (2-1) and the equation (2-2). From $V_m$, a specific surface area $a_{sBET}$ is then calculated based on the equation (3) (see, pages 62 to 66 of the manual of analysis software for BELSORP-mini and BELSORP manufactured by BEL Japan, Inc.). It is to be noted that this nitrogen BET method is a measurement method which follows JIS R 1626-1996 "Measurement method of the specific surface area of fine ceramic powder by the gas adsorption BET method."

$$V_a=(V_m \cdot C \cdot p)/[(p_0-p)\{1+(C-1)(p/p_0)\}] \quad (1)$$

$$[p/\{V_a(p_0-p)\}]=[(C-1)/(C \cdot V_m)](p/p_0)+[1/(C \cdot V_m)] \quad (1')$$

$$V_m=1/(s+i) \quad (2\text{-}1)$$

$$C=(s/i)+1 \quad (2\text{-}2)$$

$$a_{sBET}=(V_m \cdot L \cdot \sigma)/22414 \quad (3)$$

where $V_a$: Adsorbed volume
$V_m$: Adsorbed volume in a monomolecular layer
p: Pressure of nitrogen at equilibrium
$p_0$: Saturation vapor pressure of nitrogen
L: Avogadro's number
σ: Absorption cross-sectional area of nitrogen When calculating a pore volume $V_p$ by the nitrogen BET method, an adsorbed volume V at a relative pressure preset as a relative pressure for the calculation of pore volume is determined, for example, by linearly interpolating the adsorption data of a determined adsorption isotherm. From this adsorbed volume V, the pore volume $V_p$ can be calculated based on the equation (4) (see pages 62 to 65 of the Analysis Software Manual for BELSORP-mini and BELSORP manufactured by BEL Japan, Inc.). It is to be noted that a pore volume based on the nitrogen BET method may also be called simply "a pore volume."

$$V_p=(V/22414) \times (M_g/\rho_g) \quad (4)$$

where

V: Adsorbed amount at a relative pressure
$M_g$: Molecular weight of nitrogen
$\rho_g$: Density of nitrogen The pore sizes of mesopores can be calculated, for example, as a distribution of pores from a rate of change in pore volume relative to the pore sizes on the basis of the BJH method. The BJH method is a method widely employed as a pore distribution analysis method. Upon conducting a pore distribution analysis on the basis of the BJH method, a desorption isotherm is first determined by causing adsorption and desorption of nitrogen as adsorptive molecules on an adsorbent (porous carbon material composite). Based on the thus-determined desorption isotherm, the thickness of an adsorbed layer upon stepwise desorption of adsorptive molecules (for example, nitrogen) from a state that a pore is filled with the adsorptive molecules and the inner diameter of a pore (two times of the radius of the core) formed upon desorption are determined. The pore radius $r_p$ is calculated based on the equation (5), and the pore volume is calculated based on the equation (6). A pore distribution curve can then be obtained from the pore radius and pore volume by plotting the rate of change in pore volume ($dV_p/dr_p$) against the pore size ($2r_p$) (see pages 85 to 88 of the Analysis Software Manual for BELSORP-mini and BELSORP manufactured by BEL Japan, Inc.).

$$r_p=t+r_k \quad (5)$$

$$V_{pn}=R_n \cdot dV_n - R_n \cdot dt_n \cdot c \cdot \Sigma A_{pj} \quad (6)$$

$$\text{where } R_n=r_{pn}^2/(r_{kn}-1+dt_n)^2 \quad (7)$$

where $r_p$: Pore radius
$r_k$: Core diameter (inner diameter/2) when an adsorption layer of t in thickness is adsorbed at the pressure on the inner wall of a pore having a pore radius $r_p$
$V_{pn}$: pore volume when the nth desorption of nitrogen has occurred
$dV_n$: Amount of a change upon occurrence of the desorption $dt_n$: Amount of a change in the thickness $t_n$ when the nth desorption of nitrogen has occurred $r_{kn}$: core radius at the time of the nth desorption of nitrogen c: fixed value $r_{pn}$: Pore radius when the nth desorption of nitrogen has occurred.

Further, $\Sigma A_{pj}$ represents the integrated value of the areas of the walls of pores from j=1 to j=n−1.

The pore sizes of micropores can be calculated, for example, as a distribution of pores from a rate of change in pore volume relative to the pore sizes on the basis of the MP method. Upon conducting a pore distribution analysis on the basis of the MP method, an adsorption isotherm is first determined by causing adsorption of nitrogen on an adsorbent (porous carbon material composite). This adsorption isotherm is then converted into a pore volume against the thickness t of the adsorbed layer (plotted against t). Based on the curvature of the plots (the amounts of changes in pore volume relative to the amounts of changes in the thickness t of the adsorbed layer), a pore size distribution curve can then be obtained (see pages 72 to 73 and 82 of manual of analysis software for BELSORP-mini and BELSORP manufactured by BEL Japan, Inc.).

As another alternative, the porous carbon material can be formed such that it has a peak in a range of from $1\times10^{-7}$ m to $5\times10^{-6}$ m in a pore size distribution as determined by the mercury penetration method and has a peak in a range of from 2 nm to 20 nm in a pore size distribution as determined by the BJH method. The porous carbon material may preferably be formed such that it has a peak in a range of from $2\times10^{-7}$ m to $2\times10^{-6}$ m in the pore size distribution as determined by the mercury penetration method and has a peak in a range of from 2 nm to 10 nm in the pore size distribution as determined by the BJH method.

The porous carbon material precursors [1], [2] are treated with an acid or alkali. As a specific treatment method, for example, a method that immerses the porous carbon material precursors [1], [2] in aqueous solutions of the acid or alkali or a method that reacts the porous carbon material precursor [1], [2] with the acid or alkali in a vapor phase can be mentioned. More specifically, when conducting the treatment with the acid, the acid can be, for example, a fluorine compound that shows acidity, such as hydrogen fluoride, hydrofluoric acid, ammonium fluoride, calcium fluoride or sodium fluoride. When such a fluorine compound is used, the fluorine element is needed to be in an amount four times as much as the silicon element in the silicon components contained in the porous carbon material precursor [1] or [2], and the concentration of an aqueous solution of the fluorine compound may preferably be 10 wt % or higher. When eliminating, with hydrofluoric acid, the silicon components (for example, silicon dioxide) contained in the porous carbon material precursor [1] or [2], silicon dioxide reacts with hydrofluoric acid as shown by the chemical equation (A) or chemical equation (B), and is eliminated as hexafluorosilicic acid ($H_2SiF_6$) or silicon tetrafluoride ($SiF_4$) so that a porous carbon material can be obtained. It is then necessary to conduct washing and drying.

$$SiO_2 + 6HF \rightarrow H_2SiF_6 + 2H_2O \quad (A)$$

$$SiO_2 + 4HF \rightarrow SiF_4 + 2H_2O \quad (B)$$

When conducting the treatment with the alkali (base), the alkali can be sodium hydroxide. When an aqueous solution of the alkali is used, the pH of the aqueous solution is needed to be 11 or higher. When eliminating, with an aqueous solution of sodium hydroxide, the silicon components (for example, silicon dioxide) contained in the porous carbon material precursor [1] or [2], heating of the aqueous solution of sodium hydroxide causes silicon dioxide to react as indicated by the chemical equation (C) so that silicon dioxide is eliminated as sodium silicate ($Na_2SiO_3$) to obtain a porous carbon material. When sodium hydroxide is reacted in a vapor phase to conduct the treatment, on the other hand, heating of solid sodium hydroxide induces a reaction as indicated by the chemical equation (C) so that silicon dioxide is eliminated as sodium silicate ($Na_2SiO_3$) to obtain a porous carbon material. It is then necessary to conduct washing and drying.

$$SiO_2 + 2NaOH \rightarrow Na_2SiO_3 + H_2O \quad (C)$$

In addition to the above-mentioned applications, the porous carbon material composite according to the present invention can be used widely, for example, as an adsorbent for adsorbing a pigment, an adsorbent for adsorbing a toxin, a drug carrier, a water purifying agent, a soil purifying agent, a catalyst capable of promoting a specific reaction, and a kind of sensor for detecting the existence of a certain substance based on a change in color upon adsorption of the substance. Using, as functional materials, calcium carbonate, calcium acetate, a high-molecular film containing many amino groups, a monomolecular film containing many amino groups, and the like, the porous carbon material composite according to the present invention can also be used as phosphorus adsorbents and phosphorus adsorbent medicines that make use of binding between them and phosphorus. By combining, for example, with a functional (inorganic) material having magnetism, the above-described materials and the like can be recovered or moved with a magnet.

Example 1

Example 1 relates to the porous carbon material composite according to the present invention and also to the process according to the present invention for the production of a porous carbon material composite. A porous carbon material composition of Example 1 is composed of:

(A) a porous carbon material obtainable from a plant-derived material having a silicon (Si) content of 5 wt % or higher as a raw material, said porous carbon material having a silicon (Si) content of 1 wt % or lower; and (B) a functional material adhered on the porous carbon material.

The porous carbon material composite has a value of specific surface area of 10 $m^2/g$ or greater as determined by the nitrogen BET method and a pore volume of 0.1 $cm^3/g$ or greater as determined by the BJH method and MP method.

In Example 1, rice (rice plant) husks were used as a plant-derived material, that is, a raw material for a porous carbon material. The porous carbon material in Example 1 was obtained by carbonizing the rice husks as a raw material into a carbonaceous material [1] (a porous carbon material precursor [1]) and then applying an acid treatment. After the porous carbon material was obtained, the functional material was caused to adhere on the porous carbon material to obtain the porous carbon material composite. Described specifically, the functional material in Example 1 was composed of an inorganic material such as iron containing a trace amount of iron oxide ($Fe_3O_4$), and adhered in the form of fine particles on surfaces (including the interiors of pores) of the porous carbon material.

[Step 100]

In the production of the porous carbon material composite of Example 1, the plant-derived material was first carbonized at from 800° C. to 1,400° C., followed by treatment with an acid or alkali to obtain the porous carbon material. Namely, heat treatment (precarbonization treatment) was first applied to the rice husks (grown in Kagoshima Prefecture, husks of the Isehikari variety), which had been ground, in an inert gas. Specifically, the rice husks were heated and charred at 500° C. for five hours in a nitrogen gas stream to obtain a charred material. It is to be noted that by conducting such treatment, tar components which would be formed in the subsequent carbonization can be decreased or eliminated. Subsequently, a portion (10 g) of the charred material was placed in an alumina-made crucible, and was heated to 800° C. at a ramp-up rate of 5° C./min in a nitrogen gas stream (10 L/min). The charred material was then carbonized at 800° C. for one hour into a carbonaceous material [1] (porous carbon material precursor [1]), which was thereafter allowed to cool down to room temperature. It is to be noted that during the carbonization and cooling, nitrogen gas was caused to flow continuously. The porous carbon material precursor [1] was then immersed overnight in a 46 vol % aqueous solution of hydrofluoric acid to conduct its acid treatment, followed by washing with water and ethyl alcohol until pH 7 was reached. By finally conducting drying at 120° C., it was possible to obtain the porous carbon material.

[Step 110]

On the thus-obtained porous carbon material, the functional material was then caused to adhere. It is to be noted that the treatment, in which the functional material is caused to adhere on the porous carbon material, may hereinafter be called "the complexing treatment." Described specifically, after the porous carbon material was immersed at 25° C. for 24 hours in a 0.5 mol/L aqueous solution of iron chloride, the porous carbon material was washed with water and then subjected to heat treatment at 750° C. for three hours under a nitrogen atmosphere.

The same porous carbon material (which had not been subjected to the complexing treatment) as in Example 1 was provided as Comparative Example 1 for various tests.

With respect to the porous carbon material composite of Example 1 and the porous carbon material of Comparative Example 1, the values of their specific surface areas and their pore volumes were measured. The results shown in Table 1 were obtained. With respect to the porous carbon material composite of Example 1 and the porous carbon material of Comparative Example 1, the pore size distributions of their mesopores and micropores were also measured. The results shown in (A) of FIG. 1 and (B) of FIG. 1 were obtained.

Nitrogen adsorption and desorption tests were conducted using BELSORP-mini (manufactured by BEL Japan, Inc.) as a measuring instrument for the determination of the values of specific surface areas and the pore volumes. As a measuring condition, the measurement equilibrium relative pressure ($p/p_0$) was set at 0.15 to 0.975. Based on the BELSORP Analysis Software, the values of specific surface areas and the pore volumes were calculated. Further, nitrogen adsorption and desorption tests were conducted using the above-mentioned measuring instrument, and the pore size distributions of the mesopores and micropores were calculated by the BELSORP Analysis Software on the basis of the BJH method and MP method. It is to be noted that in examples and comparative examples to be described subsequently herein, the measurements of the values of specific surface areas and pore volumes and the pore size distributions of mesopores and micropores were conducted by similar methods.

The porous carbon material composite of Example 1 subjected to the complexing treatment was smaller in the value of specific surface area and pore volume than the porous carbon material of Comparative Example 1 not subjected to the complexing treatment. These results are considered to be attributable to the closure of pores of the porous carbon material by the adhesion (deposit) of the functional material (fine magnetic particles) and/or an increase in weight by the adhesion (deposit) of the functional material, both as a result of the complexing treatment.

Figure 1B:
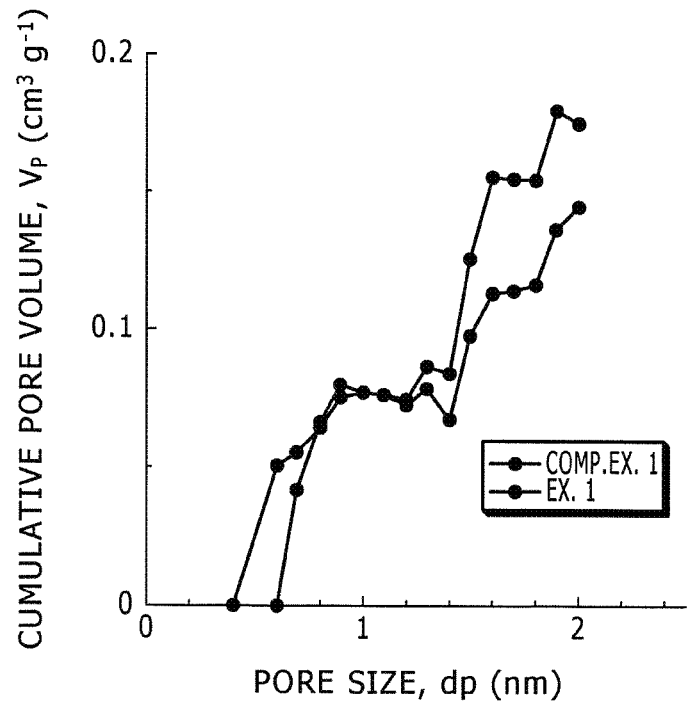

From the pore size distribution curves of (A) of FIG. 1 and (B) of FIG. 1, the pore volume is recognized to have decreased in general. Especially in the micropore range shown in (B) of FIG. 1, marked decreases in pore volume are recognized in Example 1 compared with Comparative Example 1. These decreases are considered to be attributable to the deposit of the functional material.

The porous carbon material composite of Example 1 and the porous carbon material of Comparative Example 1 were also subjected to an elemental analysis, and the results shown in Table 2 were obtained. It is to be noted that using an energy dispersive X-ray analyzer (JED-2200F manufactured by JEOL Ltd.) as a measuring instrument for elemental analyses, each element was quantitated by energy dispersion spectroscopy (EDS) and its content was then calculated in terms of percentage by weight (wt %). As measurement conditions, the scanning voltage and irradiation current were set at 15 kV and 10 μA, respectively. They were set likewise in the subsequent examples and comparative examples.

In Comparative Example 1, the content of Fe was 0.01 wt % or lower. In Example 1, on the other hand, it increased to 15.7 wt %. This increase is considered to be attributable to the deposit of iron-containing phases by the complexing treatment.

Figure 7:
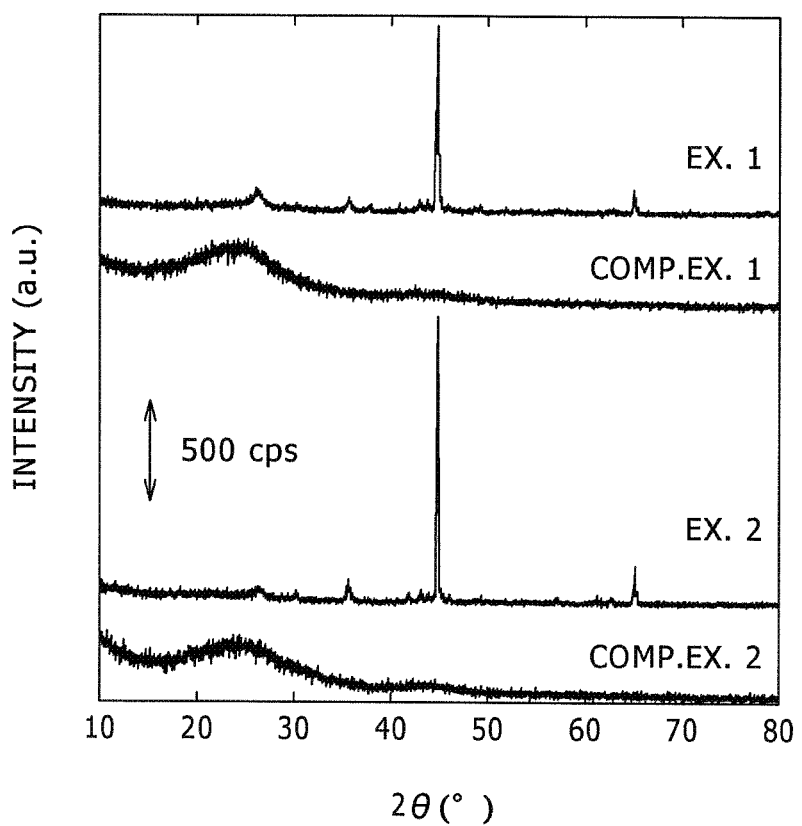
FIG. 7 is a chart of the results of X-ray diffraction of the porous carbon material composites of Example 1 and Example 2 and the porous carbon materials of Comparative Example 1 and Comparative Example 2 as obtained by powder X-ray diffractometry, respectively.

Further, the results of assessments of the porous carbon material composite of Example 1 and the porous carbon material of Comparative Example 1 by powder X-ray diffractometry are shown in FIG. 7. Here, an X-ray diffractometer (RINT-TTRII) manufactured by RIGAKU Corporation was used, and Cu—K α radiation was employed as an X-ray source. It is to be noted that the wavelength was 0.15405 nm. In addition, the applied voltage was set at 50 kilovolts, and the scanning step was set at 0.04°. Similar conditions were set for the measurements in the subsequent examples and comparative examples.

Primary phases formed in Example 1 were determined to be formed of metal iron from the X-ray diffraction pattern. In addition to metal iron, diffraction peaks ascribable to oxidized iron were also observed although they were weak. On the other hand, a broad diffraction peak from the (002) plane of carbon, which had been observed around $2\theta=24°$ before the complexing treatment (see Comparative Example 1), was observed as a relatively sharp peak around $2\theta=26°$ after the complexing treatment (see Example 1). This suggests that the formation of a layer structure in the porous carbon material was promoted by the complexing heat treatment.

Figure 10A:
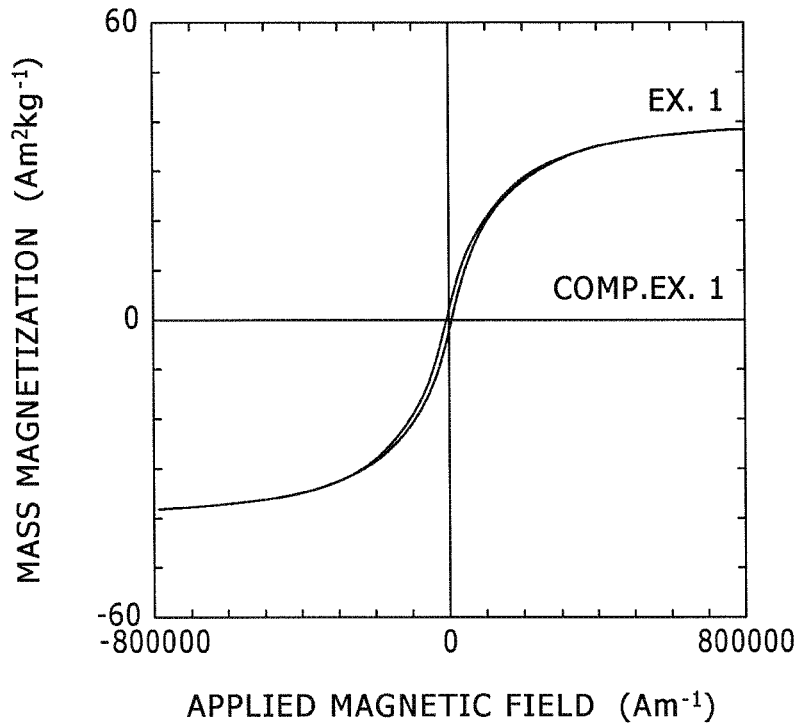
FIGS. 10(A) and 10(B) show magnetization curves of the porous carbon material composite of Example 1 and the porous carbon material of Comparative Example 1 and magnetization curves of the porous carbon material composite of Example 2 and the porous carbon material of Comparative Example 2, respectively.
Figure 10B:
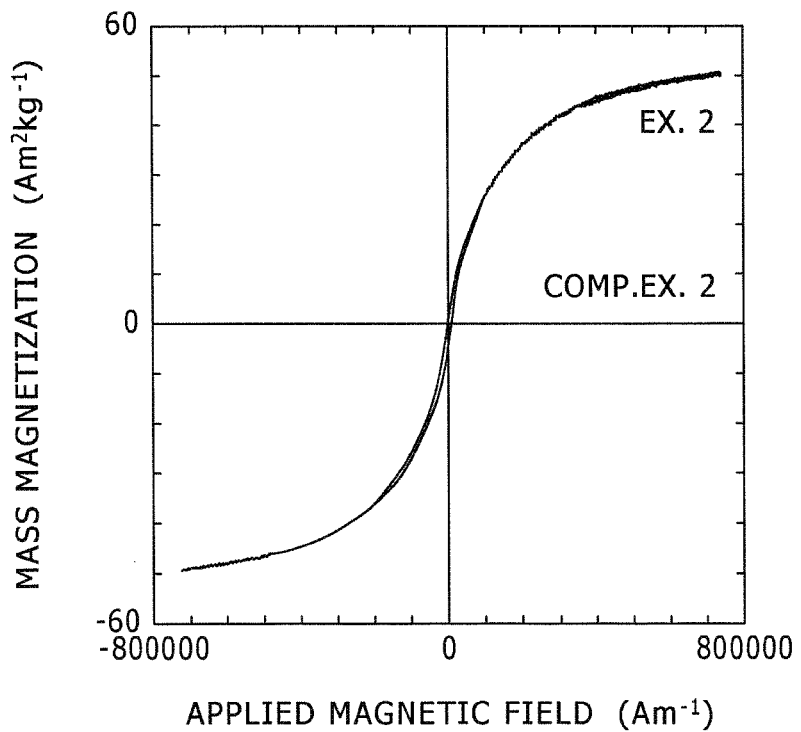

With respect to the porous carbon material composite of Example 1 and the porous carbon material of Comparative Example 1, their magnetization curves were assessed. The magnetization curves obtained are shown in (A) of FIG. 10. These magnetization curves were measured by using a sample vibrating magnetometer (Model 4500) manufactured by Lake Shore Cryotronics, Inc. The same magnetometer was used for the measurements in the subsequent examples and comparative examples.

The porous carbon material of Comparative Example 1 was substantially non-magnetic. With the porous carbon material composite of Example 1 in which the complexing treatment was conducted, a significant increase was confirmed in saturation mass magnetization and a saturation magnetization of about 38 A·m$^2$/kg was shown, thereby indicating that magnetic properties had been imparted to the porous carbon material composite.

As the content of silicon (Si) was substantially decreased in the porous carbon material composite of Example 1, it has been suggested that by treating the porous carbon material precursor [1] with the acid, the contained silicon components such as silicon dioxide are removed, thereby contributing to an increase in the value of specific surface area. It has also been confirmed that the treatment with the acid leads to increases in mesopores and micropores. These tendencies were similar in the examples to be described below. Similar results were also obtained with a porous carbon material obtained by conducting treatment with an alkali (base) such as an aqueous solution of sodium hydroxide in place of an aqueous solution of hydrofluoric acid.

The measurement results of the specific surface area and pore volume of the porous carbon material obtained in [Step 100] (hereinafter called "the porous carbon material A") were as described below. Subsequent to [Step 100], activation treatment was conducted by heating the porous carbon material in a steam stream of 900° C. for two hours to obtain another porous carbon material (hereinafter called "the porous carbon material B") and then for three hours to obtain a further porous carbon material (hereinafter called "the porous carbon material C"). The measurement results of the specific surface areas and pore volumes of the porous carbon materials B,C were as described below.

[Porous Carbon Material A]

Specific surface area: 589 m$^2$/g

Pore volume: 0.60 cm$^3$/g

[Porous Carbon Material B]

Specific surface area: 930 m$^2$/g

Pore volume: 0.80 cm$^3$/g

[Porous Carbon Material C]

Specific surface area: 1,309 m$^2$/g

Pore volume: 1.16 cm$^3$/g

Measurements were conducted to determine how much indole (number average molecular weight: 117) the porous carbon materials A,B,C would adsorb. Described specifically, using indole and a phosphate buffer of pH 7.3, a 4.234×10$^{-4}$ mol/L aqueous solution was prepared. The porous carbon materials A,B,C (0.010 g each) were separately added to aliquots (40.0 mL each) of the thus-prepared aqueous solution, followed by shaking at 37±2° C. for one hour. Subsequent to the shaking, the porous carbon materials A,B,C were separately removed from the aliquots of the aqueous solution by using membrane filters made of polytetrafluoroethylene and having a pore size of 500 μm. The absorbances of the respective filtrates were determined by UV-visible light absorbance measurement, and then, the molar concentrations of the respective aqueous solutions were determined. By comparing the molar concentrations with the molar concentration of the initial aqueous solution before the adsorption, the adsorbed amounts were calculated. Each amount adsorbed per gram of the porous carbon material was calculated based on the following equation.

(Amount adsorbed per gram of porous carbon material)=(the molecular weight of solute)×{(the molar concentration of aqueous solution before adsorption)−(the molar concentration of aqueous solution after adsorption)}/(the amount of porous carbon material per 1,000 mL)

For the sake of reference, an adsorbed amount per gram was also determined by using, as a reference example, activated carbon, that is, Kremezin (produced using petroleum pitch as a raw material; product of KUREHA CORPORATION, specific surface area: 1,079 m$^2$/g, pore volume: 0.60 cm$^3$/g).

The measurement results of the adsorbed amounts were as described below. Namely, the porous carbon materials A,B,C showed greater adsorption ability than Kremezin.

Porous carbon material A: 58.98 (mg)

Porous carbon material B: 167.25 (mg)

Porous carbon material C: 205.81 (mg)

Kremezin: 32.88 (mg)

Example 2

Example 2 is a modification of Example 1. In Example 2, activation treatment was conducted by heating the porous carbon material at 900° C. in a steam stream for three hours subsequent to [Step 100] in Example 1. After that, similar complexing treatment as in [Step 110] in Example 1 was conducted.

The same porous carbon material (which had not been subjected to the complexing treatment) as in Example 2 was provided as Comparative Example 2 for various tests.

With respect to the porous carbon material composite of Example 2 and the porous carbon material of Comparative Example 2, the values of their specific surface areas and their pore volumes were measured. The results shown in Table 1 were obtained. The pore size distributions of their mesopores and micropores were also measured. The results shown in (A) of FIG. 2 (B) of FIG. 2 were obtained.

Figure 2A:
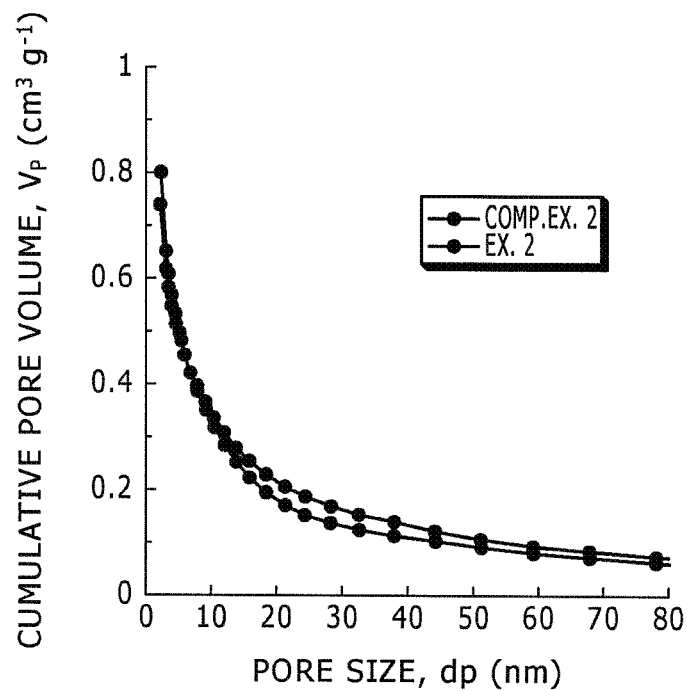
FIGS. 2(A) and 2(B) are graphs showing the pore size distributions of mesopores and the pore size distributions of micropores in a porous carbon material composite of Example 2 and a porous carbon material of Comparative Example 2, respectively.
Figure 2B:
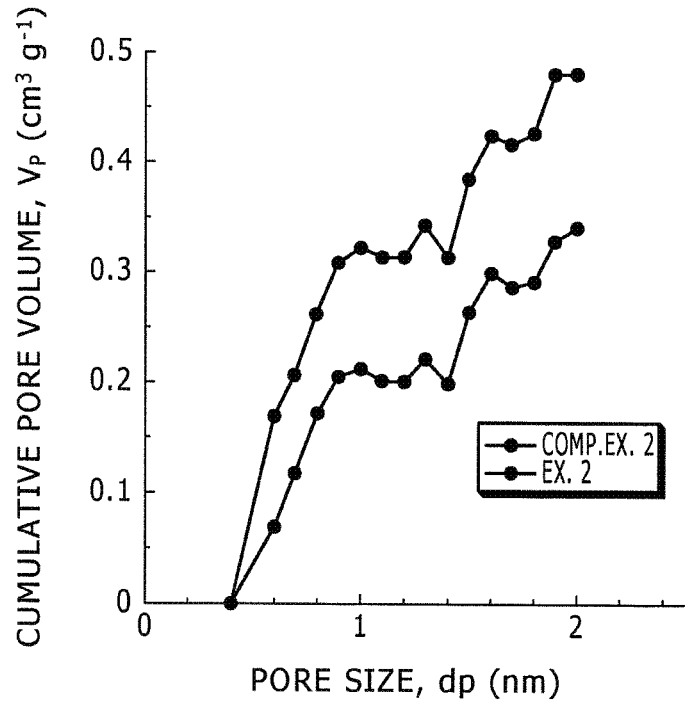

The porous carbon material composite of Example 2 subjected to the complexing treatment was greater in the value of specific surface area and pore volume than Example 1 and Comparative Example 1, but was smaller than the porous carbon material of Comparative Example 2. These results are considered to be attributable to the closure of pores of the porous carbon material by the adhesion (deposit) of the functional material (fine magnetic particles) and/or an increase in weight by the adhesion (deposit) of the functional material, both as a result of the complexing treatment. By the activation treatment, the value of specific surface area and the pore volume were increased. From the pore size distribution curves of (A) of FIG. 2 and (B) of FIG. 2, the pore volume in Example 2 is recognized to have decreased, especially in the micropore range shown in (B) of FIG. 2, compared with that in Comparative Example 2. These decreases are considered to be attributable to the deposit of the functional material.

The porous carbon material composite of Example 2 and the porous carbon material of Comparative Example 2 were also subjected to an elemental analysis, and the results shown in Table 2 were obtained. In Comparative Example 2, the content of Fe was 0.13 wt %. In Example 2, on the other hand, it increased to 11.4 wt %. This increase is considered to be attributable to the deposit of iron-containing phases by the complexing treatment.

Further, the results of assessments of the porous carbon material composite of Example 2 and the porous carbon material of Comparative Example 2 by powder X-ray diffractometry are shown in FIG. 7. Primary phases formed in Example 2 were determined to be formed of metal iron from the X-ray diffraction pattern. In addition to metal iron, diffraction peaks ascribable to oxidized iron were also observed although they were weak. On the other hand, a broad diffraction peak from the (002) plane of carbon, which had been observed around 2θ=24° before the complexing treatment (see Comparative Example 2), was observed as a relatively sharp peak around 2θ=26° after the complexing treatment (see Example 2). This suggests that the formation of a layer structure in the porous carbon material was promoted by the complexing heat treatment.

With respect to the porous carbon material composite of Example 2 and the porous carbon material of Comparative Example 2, their magnetization curves were assessed. The magnetization curves obtained are shown in (B) of FIG. 10. The porous carbon material of Comparative Example 2 was substantially non-magnetic. With the porous carbon material composite of Example 2 in which the complexing treatment was conducted, on the other hand, a significant increase was confirmed in saturation mass magnetization and a saturation magnetization of about 50 $A·m^2/kg$ was shown, thereby indicating that magnetic properties had been imparted to the porous carbon material composite.

Example 3

Example 3 is also a modification of Example 1. In Example 3, a functional material was made of a metal, specifically gold (Au), more specifically gold nanoparticles. In Example 3, after [Step 100] in Example 1 was conducted, the functional material was caused to adhere on the resultant porous carbon material. Described specifically, after the porous carbon material was charged as complexing treatment in a 0.25 mol/L aqueous solution of chlorauric acid, said aqueous solution containing sodium citrate at a concentration of 0.875 mol/L, the resulting mixture was boiled for 20 minutes. Subsequently, the resulting porous carbon material composite was collected by filtration, and was thoroughly washed with water.

The same porous carbon material (which had not been subjected to the complexing treatment) as in Example 3 was provided as Comparative Example 3 for various tests.

Figure 3A:
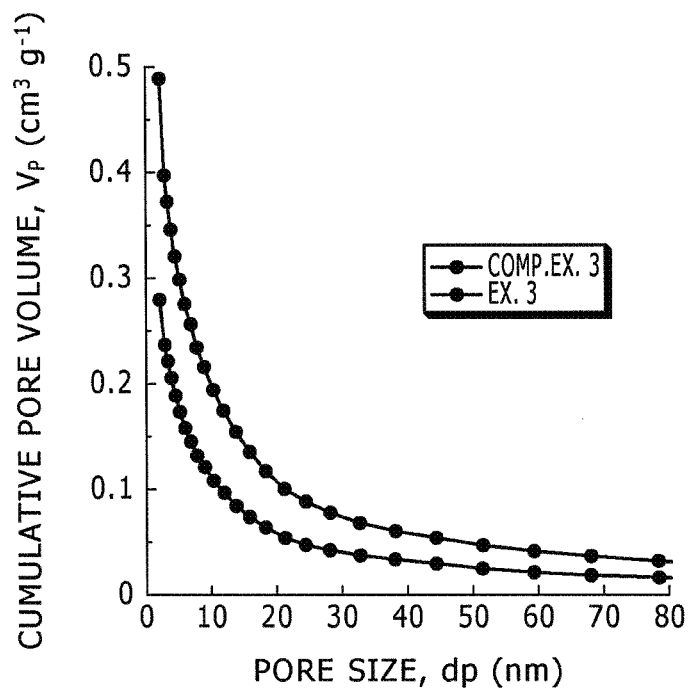
FIGS. 3(A) and 3(B) are graphs showing the pore size distributions of mesopores and the pore size distributions of micropores in a porous carbon material composite of Example 3 and a porous carbon material of Comparative Example 3, respectively.
Figure 3B:
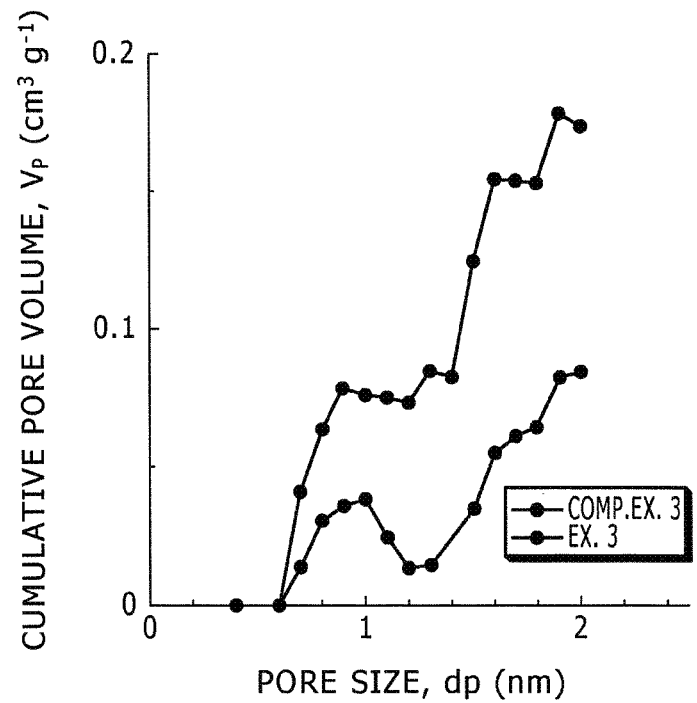

With respect to the porous carbon material composite of Example 3 and the porous carbon material of Comparative Example 3, the values of their specific surface areas and their pore volumes were measured. The results shown in Table 1 were obtained. The pore size distributions of their mesopores and micropores were also measured. The results shown in (A) of FIG. 3 and (B) of FIG. 3 were obtained.

The porous carbon material composite of Example 3 subjected to the complexing treatment was smaller in the value of specific surface area and pore volume than the porous carbon material of Comparative Example 3. These results are considered to be attributable to the closure of pores of the porous carbon material by the adhesion (deposit) of the functional material (gold nanoparticles) and/or an increase in weight by the adhesion (deposit) of the functional material, both as a result of the complexing treatment. From the pore size distribution curves of (A) of FIG. 3 and (B) of FIG. 3, the pore volume in Example 3 is recognized to have decreased over the entire pore size range compared with that in Comparative Example 3. These decreases are considered to be attributable to the deposit of gold nanoparticles.

The porous carbon material composite of Example 3 and the porous carbon material of Comparative Example 3 were also subjected to an elemental analysis, and the results shown in Table 2 were obtained. In Comparative Example 3, the content of Au was 0.01 wt % or lower. In Example 3, on the other hand, it increased to 11.5 wt %. This increase is considered to be attributable to the deposit of gold nanoparticles on the surfaces of the porous carbon material by the complexing treatment.

Figure 8:
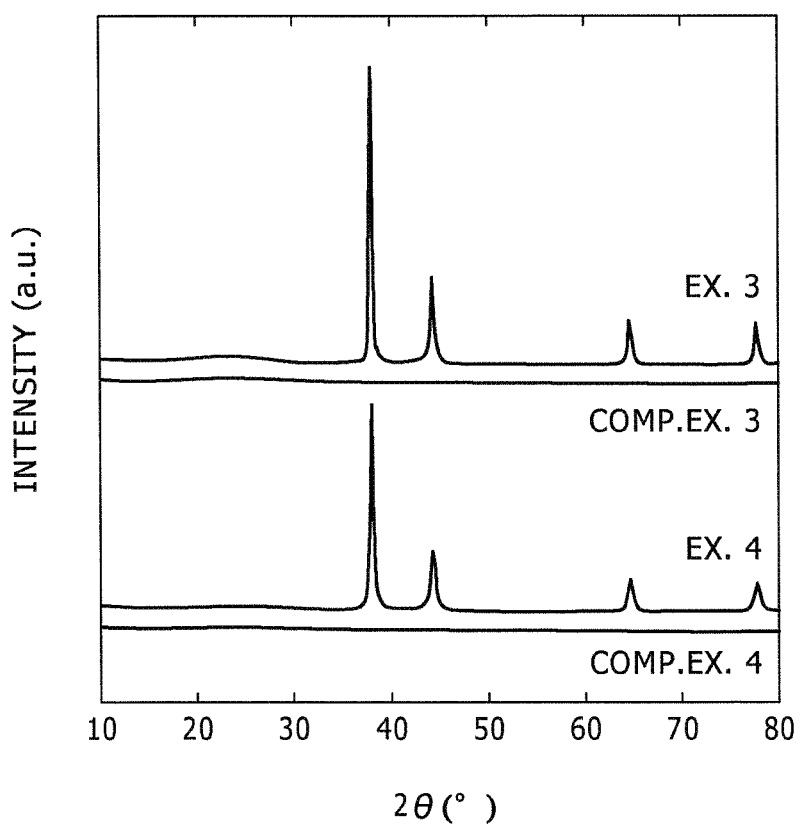
FIG. 8 is a chart of the results of X-ray diffraction of the porous carbon material composites of Example 3 and Example 4 and the porous carbon materials of Comparative Example 3 and Comparative Example 4 as obtained by powder X-ray diffractometry, respectively.

Further, the results of assessments of the porous carbon material composite of Example 3 and the porous carbon material of Comparative Example 3 by powder X-ray diffractometry are shown in FIG. 8. Primary phases formed in Example 3 were determined to be formed of gold from the X-ray diffraction pattern.

Figure 11A:
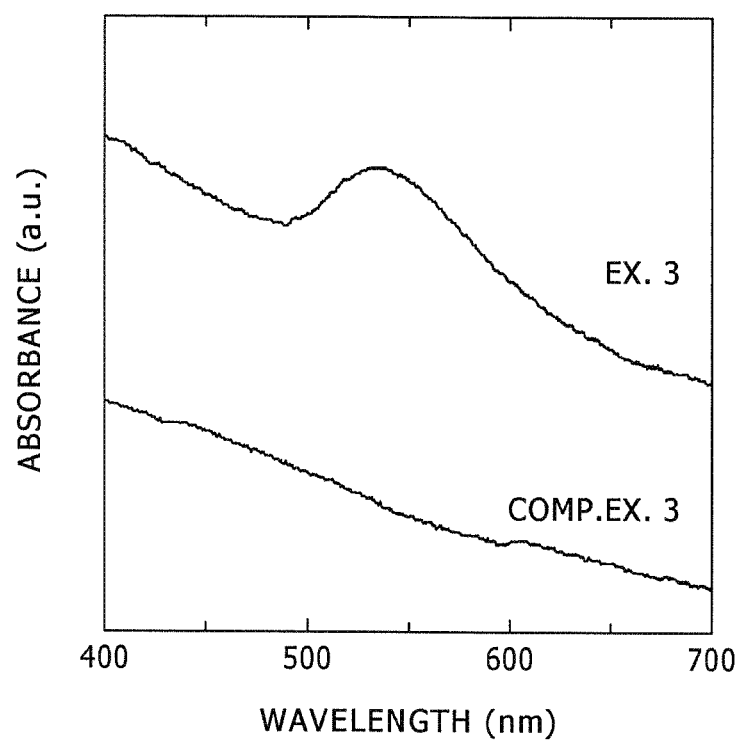
FIGS. 11(A) and 11(B) are a graph showing ultraviolet-visible absorption spectra of the porous carbon material composite of Example 3 and the porous carbon material of Comparative Example 3 and a graph showing ultraviolet-visible absorption spectra of the porous carbon material composite of Example 4 and the porous carbon material of Comparative Example 4, respectively.
Figure 11B:
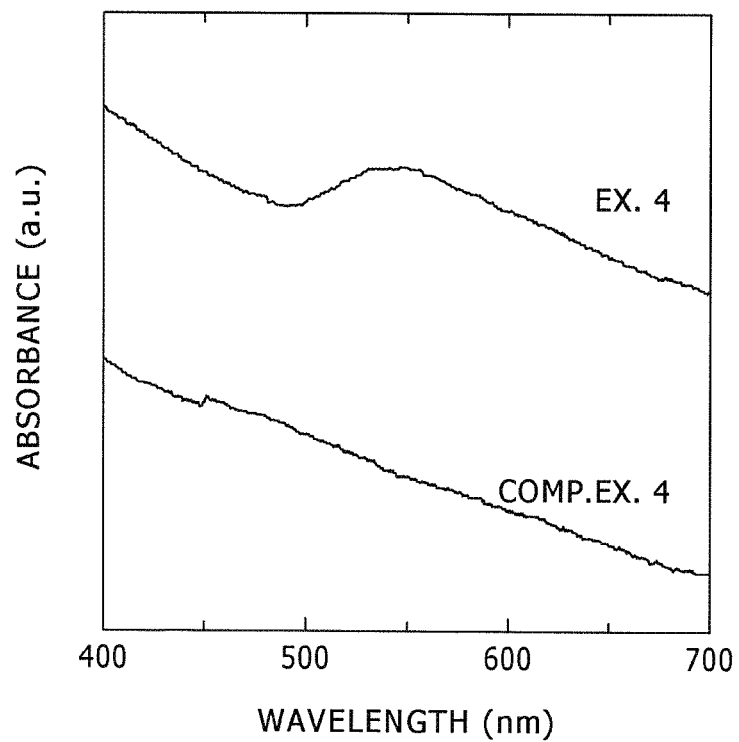

The results of assessments of ultraviolet-visible absorption spectra are shown in (A) of FIG. 11. Around 530 nm, an absorption band considered to be ascribable to surface plasmon absorption characteristic to gold nanoparticles was confirmed. From the absorption band, it was also indicated that gold nanoparticles deposited on the surfaces of the porous carbon material to form a porous carbon material composite.

Example 4

Example 4 is a modification of Example 3. In Example 4, activation treatment was conducted by heating the porous carbon material at 900° C. in a steam stream for three hours before complexing treatment. After that, similar complexing treatment as in Example 3 was conducted.

The same porous carbon material (which had not been subjected to the complexing treatment) as in Example 4 was provided as Comparative Example 4 for various tests.

Figure 4A:
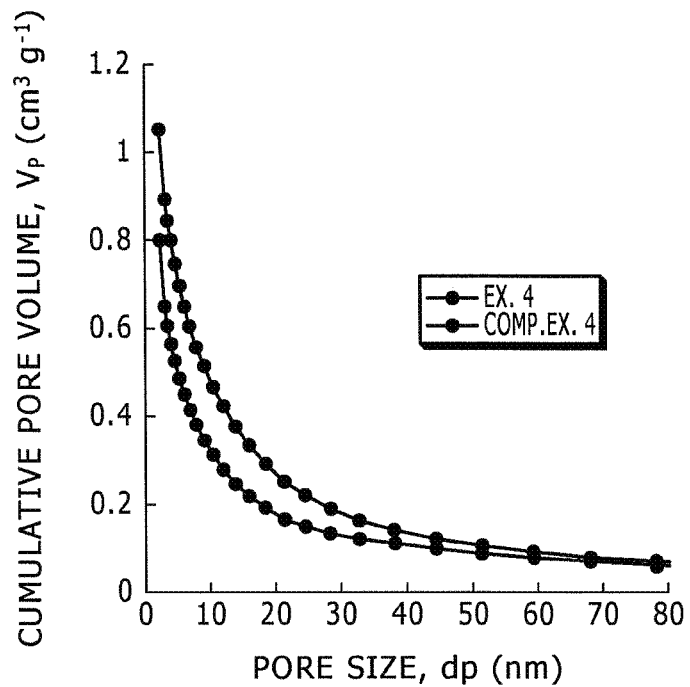
FIGS. 4(A) and 4(B) are graphs showing the pore size distributions of mesopores and the pore size distributions of micropores in a porous carbon material composite of Example 4 and a porous carbon material of Comparative Example 4, respectively.
Figure 4B:
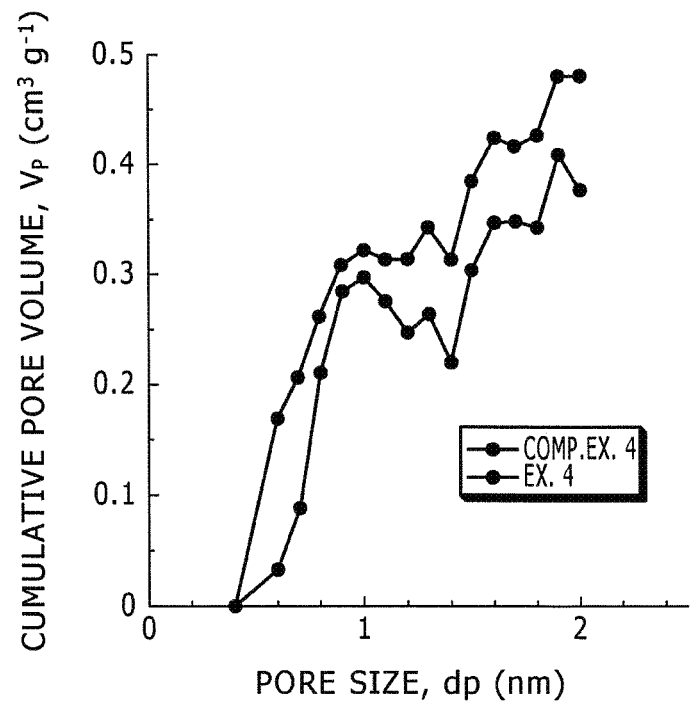

With respect to the porous carbon material composite of Example 4 and the porous carbon material of Comparative Example 4, the values of their specific surface areas and their pore volumes were measured. The results shown in Table 1 were obtained. The pore size distributions of their mesopores and micropores were also measured. The results shown in (A) of FIG. 4 and (B) of FIG. 4 were obtained.

The porous carbon material composite of Example 4 subjected to the complexing treatment was comparable in the value of specific surface area and pore volume to Comparative Example 4. From the pore size distribution curves of (A) of FIG. 4 and (B) of FIG. 4, the pore volume is recognized to have decreased, especially in the micropore range in Example 4 compared with Comparative Example 4. These decreases are considered to be attributable to the adhesion (deposit) of gold nanoparticles.

The porous carbon material composite of Example 4 and the porous carbon material of Comparative Example 4 were also subjected to an elemental analysis, and the results shown in Table 2 were obtained. In Comparative Example 4, the content of Au was 0.76 wt %. In Example 4, on the other hand, it increased to 14.0 wt %.

Further, the results of assessments of the porous carbon material composite of Example 4 and the porous carbon material of Comparative Example 4 by powder X-ray diffractometry are shown in FIG. 8. Primary phases formed in Example 4 were determined to be formed of gold from the X-ray diffraction pattern.

The results of assessments of ultraviolet-visible absorption spectra are shown in (B) of FIG. 11. Around 530 nm, an absorption band considered to be ascribable to surface plasmon absorption characteristic to gold nanoparticles was confirmed. From the absorption band, it was also indicated that gold nanoparticles deposited on the surfaces of the porous carbon material to form a porous carbon material composite.

Example 5

Example 5 is also a modification of Example 1. In Example 5, a functional material was composed of a magnetic material and also an alloy, specifically thin films of an Fe—Co—Ni alloy. In Example 5, after [Step 100] in Example 1 was conducted, the functional material was caused to adhere on the resultant porous carbon material. Described specifically, as complexing treatment, the porous carbon material was immersed for 60 seconds in dilute hydrochloric acid of 25° C., which contained palladium chloride at a concentration of 0.6 mol/L. The resulting porous carbon material composite was then washed with water. Subsequently, the porous carbon material composite was immersed for 30 minutes in an aqueous solution of 80° C., which contained cobalt sulfate (0.036 mol/L), nickel sulfate (0.004 mol/L), iron sulfate (0.06 mol/L) and dimethylamine borane (0.15 mol/L mol/L). Based on an electrolysis reaction, the thin films of the Co—Ni—Fe alloy were caused to deposit on the surfaces of the porous carbon material. After that, the resulting porous carbon material composite was thoroughly washed with water. For the details of such a process, reference may be made to Electrochemica Acta, 53, 285 to 289 (2007).

The same porous carbon material (which had not been subjected to the complexing treatment) as in Example 5 was provided as Comparative Example 5 for various tests.

Figure 5A:
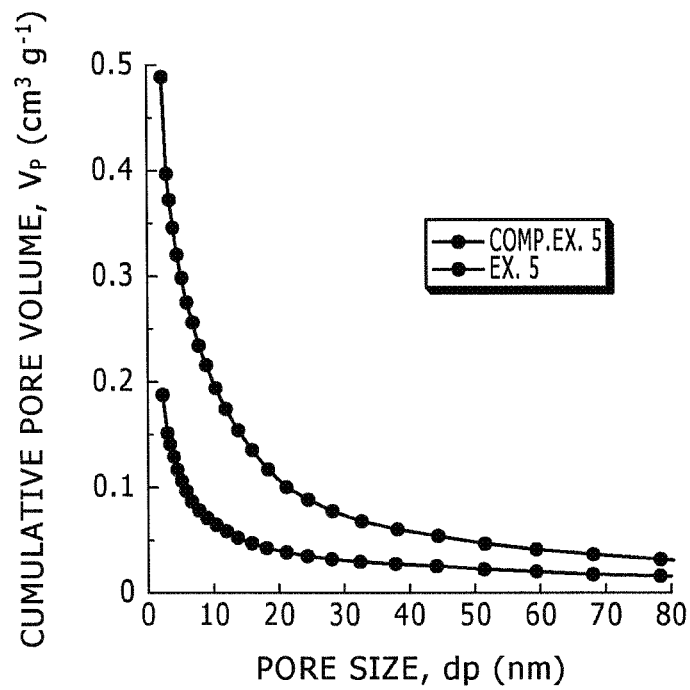
FIGS. 5(A) and 5(B) are graphs showing the pore size distributions of mesopores and the pore size distributions of micropores in a porous carbon material composite of Example 5 and a porous carbon material of Comparative Example 5, respectively.
Figure 5B:
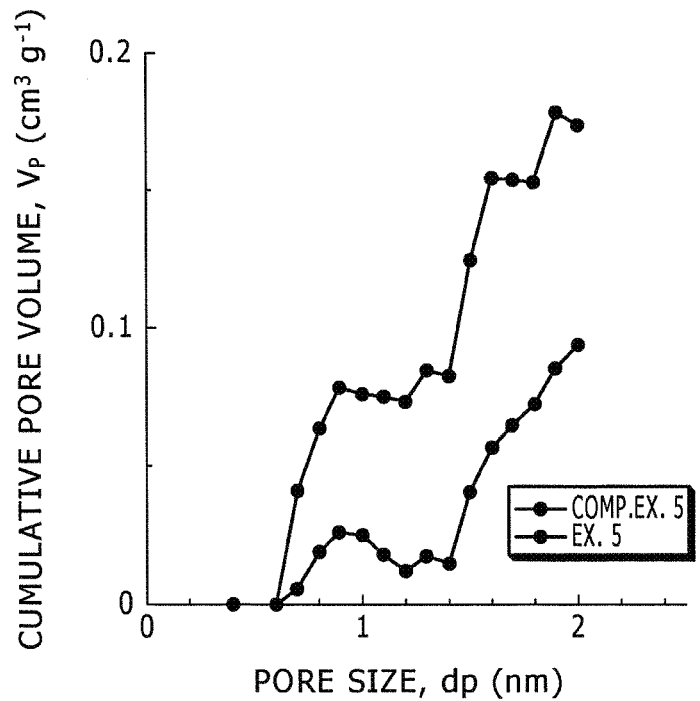

With respect to the porous carbon material composite of Example 5 and the porous carbon material of Comparative Example 5, the values of their specific surface areas and their pore volumes were measured. The results shown in Table 1 were obtained. The pore size distributions of their mesopores and micropores were also measured. The results shown in (A) of FIG. 5 and (B) of FIG. 5 were obtained. The porous carbon material composite of Example 5 subjected to the complexing treatment was smaller in the value of specific surface area and pore volume than the porous carbon material of Comparative Example 5. These results are considered to be attributable to the closure of pores of the porous carbon material by the adhesion (deposit) of the functional material (thin Co—Ni—Fe alloy films) and/or an increase in weight by the adhesion (deposit) of the functional material, both as a result of the complexing treatment. From the pore size distribution curves of (A) of FIG. 5 and (B) of FIG. 5, the pore volume in Example 5 is recognized to have decreased over the entire pore size range compared with that in Comparative Example 5. These decreases are considered to be attributable to the deposit of the functional material (thin Co—Ni—Fe alloy films).

The porous carbon material composite of Example 5 and the porous carbon material of Comparative Example 5 were also subjected to an elemental analysis, and the results shown in Table 2 were obtained. In Comparative Example 5, the contents of Co, Ni and Fe were lower than 1 wt %. In Example 5, on the other hand, the weight percentages of Co, Ni and Fe were greater. These greater weight percentages are considered to be attributable to the deposit of thin Co—Ni—Fe gold films on the surfaces of the porous carbon material by the complexing treatment.

Figure 9:
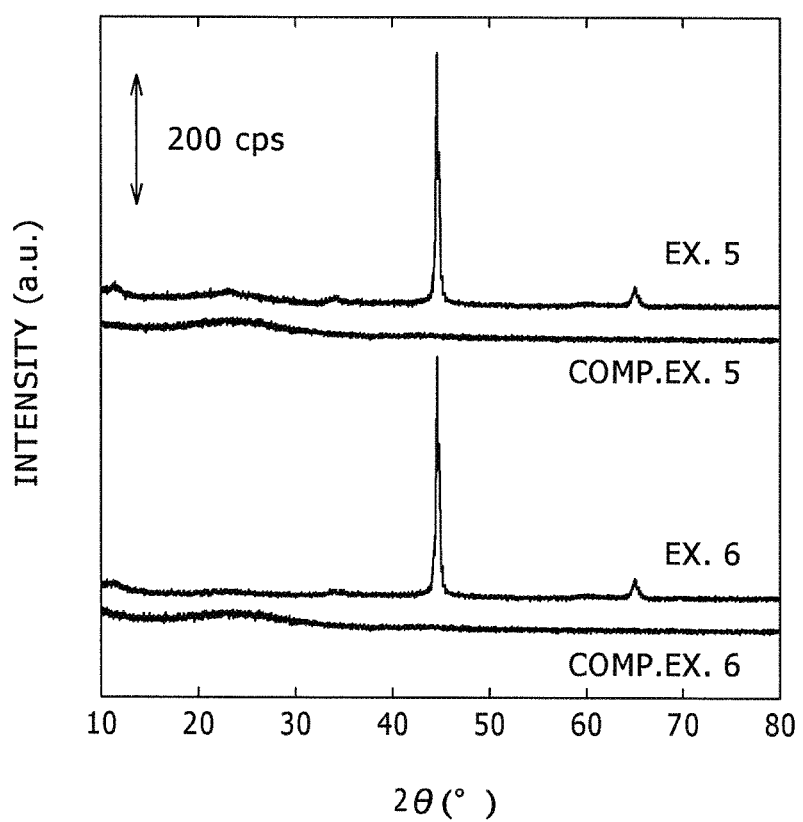
FIG. 9 is a chart of the results of X-ray diffraction of the porous carbon material composites of Example 5 and Example 6 and the porous carbon materials of Comparative Example 5 and Comparative Example 6 as obtained by powder X-ray diffractometry, respectively.

Further, the results of assessments of the porous carbon material composite of Example 5 and the porous carbon material of Comparative Example 5 by powder X-ray diffractometry are shown in FIG. 9. Primary phases formed in Example 5 were determined to be formed of the Co—Ni—Fe alloy from the X-ray diffraction pattern.

Figure 12A:
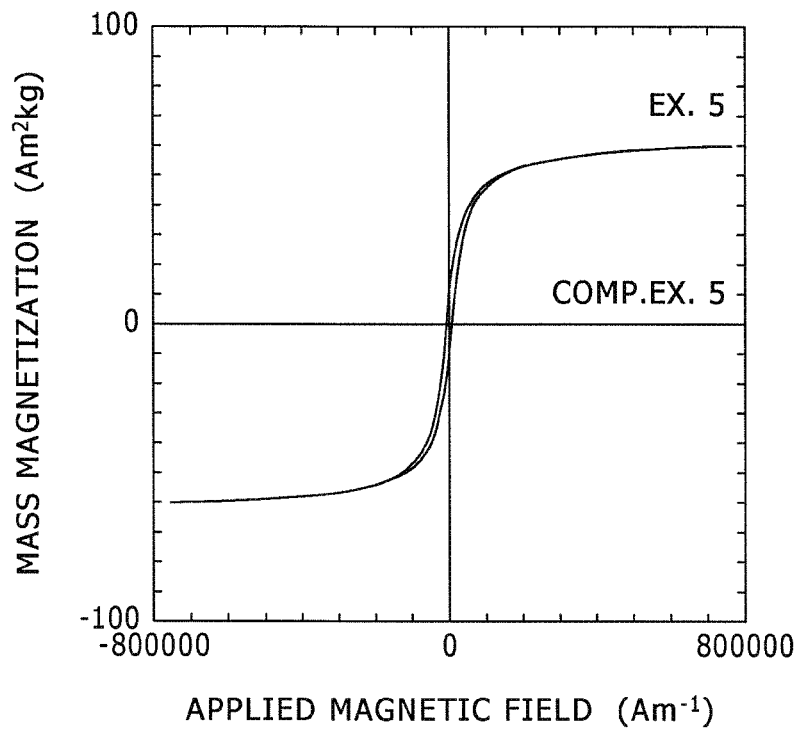
FIGS. 12(A) and 12(B) are a graph showing magnetization curves of the porous carbon material composite of Example 5 and the porous carbon material of Comparative Example 5 and a graph showing magnetization curves of the porous carbon material composite of Example 6 and the porous carbon material of Comparative Example 6, respectively.
Figure 12B:
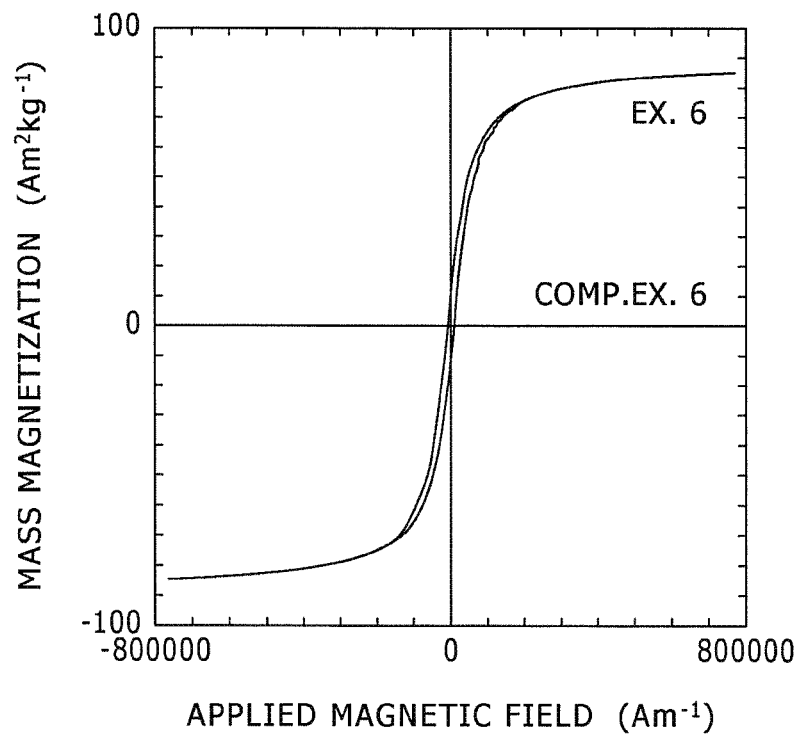
Figure 13B:
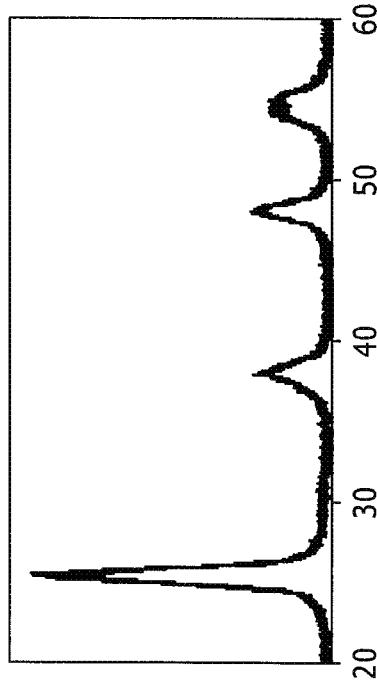
FIGS. 13(A), 13(B), 13(C) and 13(D) are charts of the results of X-ray diffraction of Referential Example 7, $TiO_2$, Example 7-A and Example 7-B as obtained by powder X-ray diffractometry, respectively.
Figure 13D:
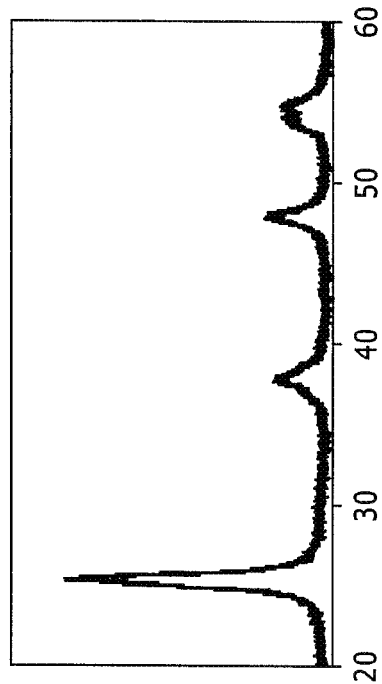
Figure 13A:
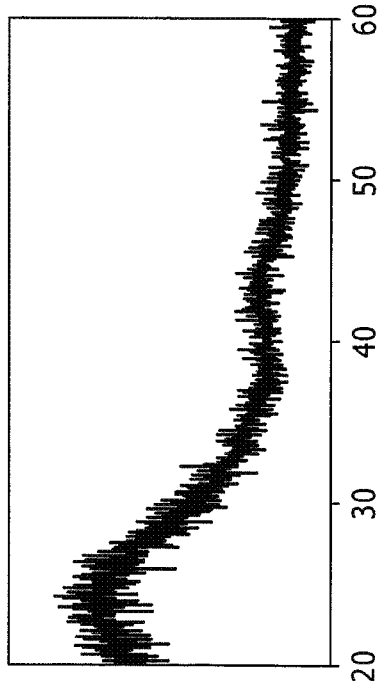
Figure 13C:
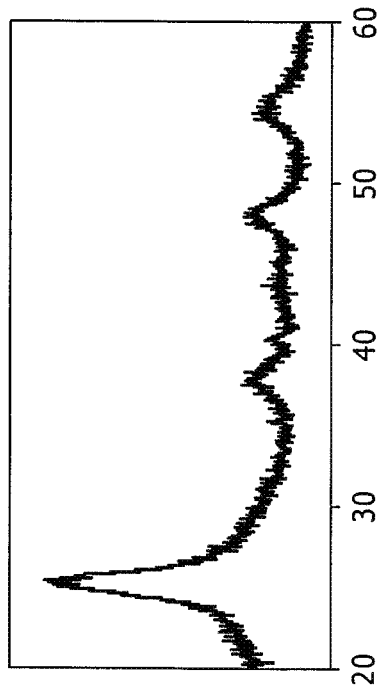

With respect to the porous carbon material composite of Example 5 and the porous carbon material of Comparative Example 5, their magnetization curves were assessed. The magnetization curves obtained are shown in (A) of FIG. 12. The porous carbon material of Comparative Example 5 was substantially non-magnetic. With the porous carbon material composite of Example 5 in which the complexing treatment was conducted, a significant increase was confirmed in saturation mass magnetization and a saturation magnetization of about 60 A·m$^2$/kg was shown, thereby indicating that magnetic properties had been imparted to the porous carbon material composite.

Example 6

Example 6 is a modification of Example 5. In Example 6, activation treatment was conducted by heating the porous carbon material at 900° C. in a steam stream for three hours before complexing treatment. After that, similar complexing treatment as in Example 5 was conducted.

The same porous carbon material (which had not been subjected to the complexing treatment) as in Example 6 was provided as Comparative Example 6 for various tests.

Figure 6A:
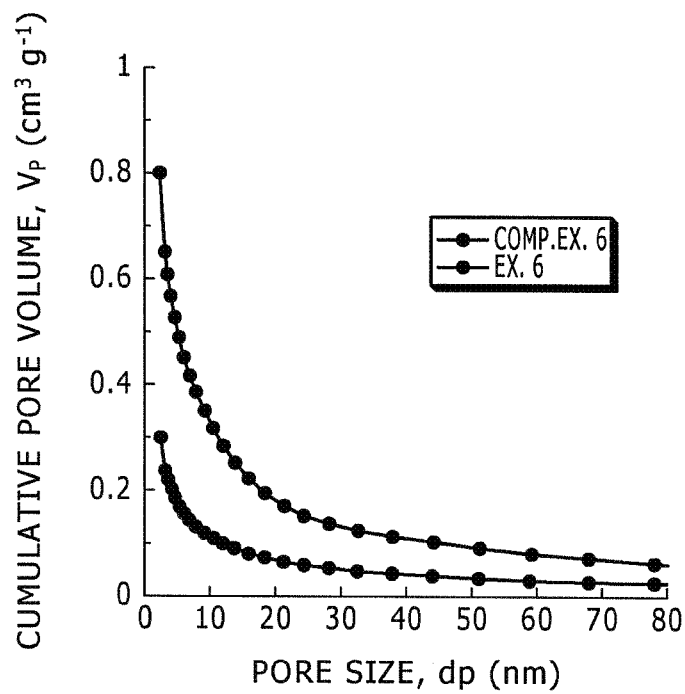
FIGS. 6(A) and 6(B) are graphs showing the pore size distributions of mesopores and the pore size distributions of micropores in a porous carbon material composite of Example 6 and a porous carbon material of Comparative Example 6, respectively.
Figure 6B:
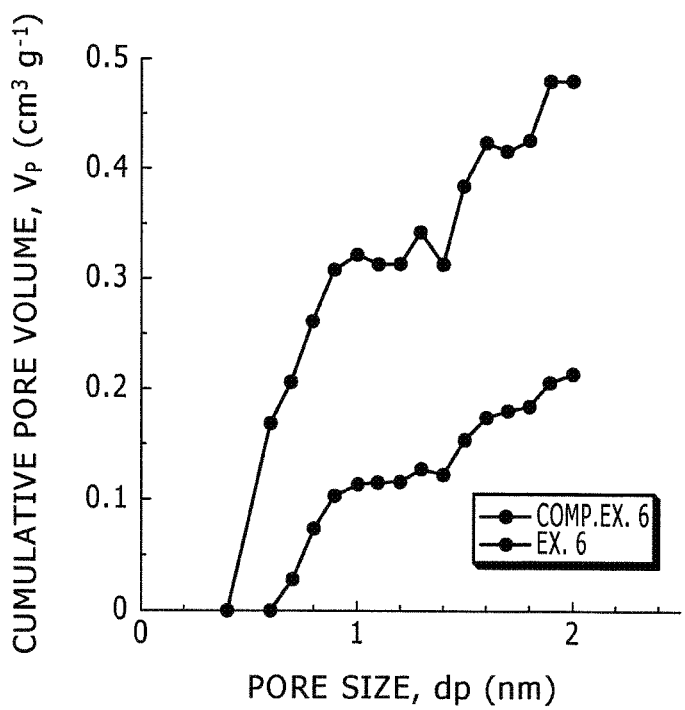

With respect to the porous carbon material composite of Example 6 and the porous carbon material of Comparative Example 6, the values of their specific surface areas and their pore volumes were measured. The results shown in Table 1 were obtained. The pore size distributions of their mesopores and micropores were also measured. The results shown in (A) of FIG. 6 and (B) of FIG. 6 were obtained. The porous carbon material composite of Example 6 subjected to the complexing treatment was smaller in the value of specific surface area and pore volume than Comparative Example 6. These results are considered to be attributable to the closure of pores of the porous carbon material by the adhesion (deposit) of the functional material (thin Co—Ni—Fe alloy films) and/or an increase in weight by the adhesion (deposit) of the functional material, both as a result of the complexing treatment. From the pore size distribution curves of (A) of FIG. 6 and (B) of FIG. 6, the pore volume in Example 6 is recognized to have decreased over the entire micropore range compared with that in Comparative Example 6. These decreases are considered to be attributable to the deposit of the functional material (thin Co—Ni—Fe alloy films).

The porous carbon material composite of Example 6 and the porous carbon material of Comparative Example 6 were also subjected to an elemental analysis, and the results shown in Table 2 were obtained. In Comparative Example 6, the contents of Co, Ni and Fe were lower than 1 wt %. In Example 6, on the other hand, the weight percentages of Co, Ni and Fe were greater. These greater weight percentages are considered to be attributable to the deposit of thin Co—Ni—Fe films on the surfaces of the porous carbon material by the complexing treatment.

Further, the results of assessments of the porous carbon material composite of Example 6 and the porous carbon material of Comparative Example 6 by powder X-ray diffractometry are shown in FIG. 9. Primary phases formed in Example 6 were determined to be formed of the Co—Ni—Fe alloy from the X-ray diffraction pattern.

With respect to the porous carbon material composite of Example 6 and the porous carbon material of Comparative Example 6, their magnetization curves were assessed. The magnetization curves obtained are shown in (B) of FIG. 12. The porous carbon material of Comparative Example 6 was substantially non-magnetic. With the porous carbon material composite of Example 6 in which the complexing treatment was conducted, on the other hand, a significant increase was confirmed in saturation mass magnetization and a saturation magnetization of about 85 A·m$^2$/kg was shown, thereby indicating that magnetic properties had been imparted to the porous carbon material composite.

TABLE 1

| Example | Comparative Example | BET specific surface area m$^2$/g | Pore volume cm$^3$/g |
|---|---|---|---|
| 1 |   | 446 | 0.5042 |
|   | 1 | 566 | 0.6046 |
| 2 |   | 999 | 0.9919 |
|   | 2 | 1,300 | 1.1636 |
| 3 |   | 282 | 0.3319 |
|   | 3 | 566 | 0.6046 |
| 4 |   | 1,320 | 1.3879 |
|   | 4 | 1,300 | 1.1636 |
| 5 |   | 208 | 0.2292 |
|   | 5 | 566 | 0.6046 |
| 6 |   | 478 | 0.4353 |
|   | 6 | 1,300 | 1.1636 |

TABLE 2

| Example | Comparative Example | C | O | Si | Fe | Co | Ni | Au |
|---|---|---|---|---|---|---|---|---|
| 1 |   | 76.0 | 3.71 | 0.43 | 15.7 | <0.01 | 0.12 | <0.01 |
|   | 1 | 84.6 | 8.83 | 0.47 | <0.01 | <0.01 | 0.81 | <0.01 |
| 2 |   | 79.6 | 1.33 | 0.72 | 11.4 | <0.01 | 0.38 | 0.62 |
|   | 2 | 86.6 | 5.91 | 1.00 | 0.13 | 0.10 | 0.08 | 0.76 |
| 3 |   | 79.0 | 1.89 | 0.42 | 0.19 | 0.21 | 0.46 | 11.5 |
|   | 3 | 84.6 | 8.83 | 0.47 | <0.01 | <0.01 | 0.81 | <0.01 |
| 4 |   | 75.4 | 2.87 | 2.13 | 0.29 | 0.30 | 0.44 | 14.0 |
|   | 4 | 86.6 | 5.91 | 1.00 | 0.13 | 0.10 | 0.08 | 0.76 |
| 5 |   | 47.7 | 4.56 | <0.01 | 22.2 | 17.4 | 4.52 | <0.01 |
|   | 5 | 84.6 | 8.83 | 0.47 | <0.01 | <0.01 | 0.81 | <0.01 |
| 6 |   | 38.5 | 4.30 | 0.27 | 19.7 | 18.4 | 5.63 | 0.86 |
|   | 6 | 86.6 | 5.91 | 1.00 | 0.13 | 0.10 | 0.08 | 0.76 |

Example 7

Example 7 is also a modification of Example 1, and relates to a composite photocatalyst material according to the present invention and a purification agent according to the present invention. The composite photocatalyst material and purification agent of Example 7 contained a porous carbon material composite each composed of:

(A) a porous carbon material obtainable from a plant-derived material having a silicon content of 5 wt % or higher as a raw material, said porous carbon material having a silicon content of 1 wt % or lower; and (B) a photocatalyst material adhered on the porous carbon material, wherein the porous carbon material composite had a specific surface area of 10 m$^2$/g or greater as determined by the nitrogen BET method and a pore volume of 0.1 cm$^3$/g or greater as determined by the BJH method and MP method.

In Example 7, the photocatalyst material or the functional material was composed of titanium oxide (TiO$_2$) that functions as a photocatalyst. In the form of particles, the titanium oxide was in adherence to the porous carbon material. Therefore, a charge separation, ultraviolet absorption property and catalytic property was imparted to the porous carbon material composite. Owing to a photocatalytic effect, the porous carbon material composite can be employed as a toxic substance decomposing agent or toxic substance removing agent which is semi-permanently usable.

In Example 7, the functional material was caused to adhere on the porous carbon material C described in Example 1. Described specifically, the complexing treatment was conducted as will be described hereinafter. Namely, the porous carbon material (0.5 g), acetic acid (4.57 mL) and tetraisopropyl orthotitanate (TIPO; as much as sufficed) were added to ethanol (100 mL), followed by stirring for one hour. Subsequently, centrifugation was conducted, and the supernatant was discarded. A small amount of ethanol was added to the solid phase, and under ultra-sonication, the resulting mixture was added little by little to purified water (100 mL). Subsequently, centrifugation was conducted again, and the resultant solid phase was dried at 100° C. Finally, crystals were allowed to grow at 400° C., thereby making it possible to obtain, as porous carbon material composites, the composite photocatalyst material and purification agent of Example 7. It is to be noted that in Example 7, two kinds of samples were obtained as Examples 7-A and 7-B. The sample of Example 7-A was obtained by adding TIPO (23.44 mL) and then conducting crystal growth in a nitrogen gas atmosphere, while the sample of Example 7-B was obtained by adding TIPO (46.88 mL) and then conducting crystal growth in air.

As a result of X-ray diffraction (XRD), TiO$_2$ was confirmed to be contained in the samples of Example 7-A and Example 7-B. (C), (D), (A) and (B) of FIG. 13 show the results of X-ray diffraction, as obtained by powder X-ray diffractometry, of the porous carbon materials in Examples 7-A, 7-B and 7-C (i.e., the porous carbon material C described in Example 1; hereinafter called "Referential Example 7") and TiO$_2$ used in Example 7.

Figure 14A:
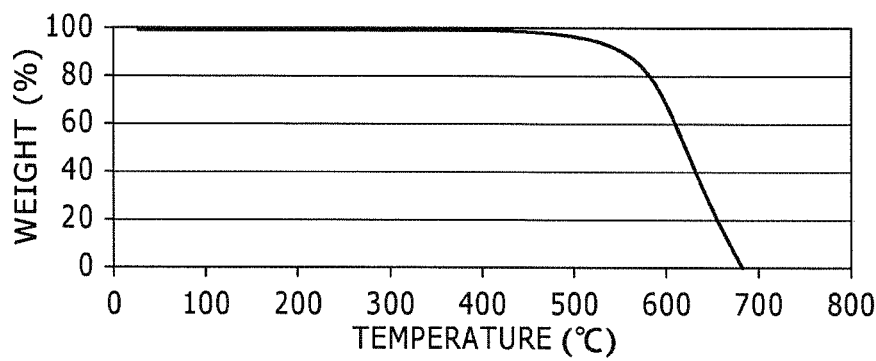
FIGS. 14(A), 14(B) and 14(C) are graphs showing the results of differential thermal analyses of Referential Example 7, Example 7-A and Example 7-B, respectively.
Figure 14B:
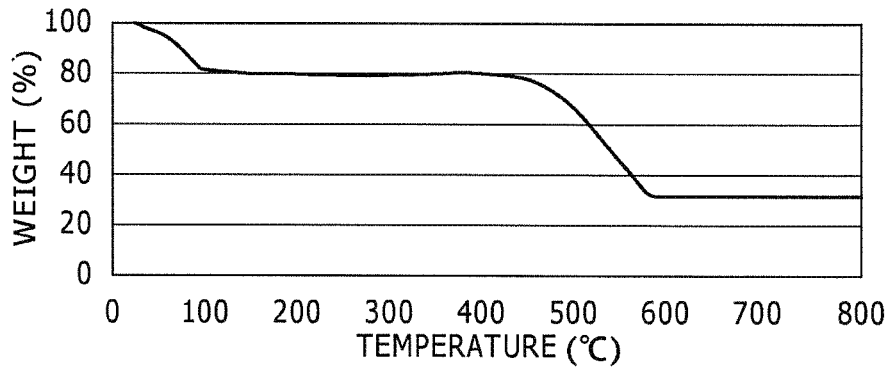
Figure 14C:
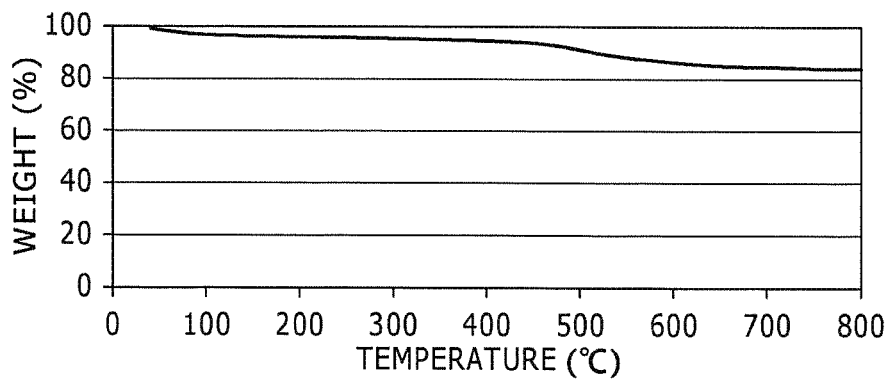

The results of measurements of TiO$_2$ contents in the samples of Examples 7-A and 7-B by the differential thermal analysis (TG) method will be shown below in Table 3. The results of differential thermal analyses of the samples of Examples 7-A and 7-B and Referential Example 7 are shown in (B), (C) and (A) of FIG. 14. The results of measurements of their specific surface areas and total pore volumes by the nitrogen BET method, BJH method and MP method will be shown below in Table 3.

TABLE 3

|  | Example 7-A | Example 7-B |
|---|---|---|
| $TiO_2$ content (wt %) | 33.3 | 85.5 |
| Specific surface area (m²/g) | 962 | 196 |
| Total pore volume (m³/g) | 0.813 | 0.405 |

Figure 15A:
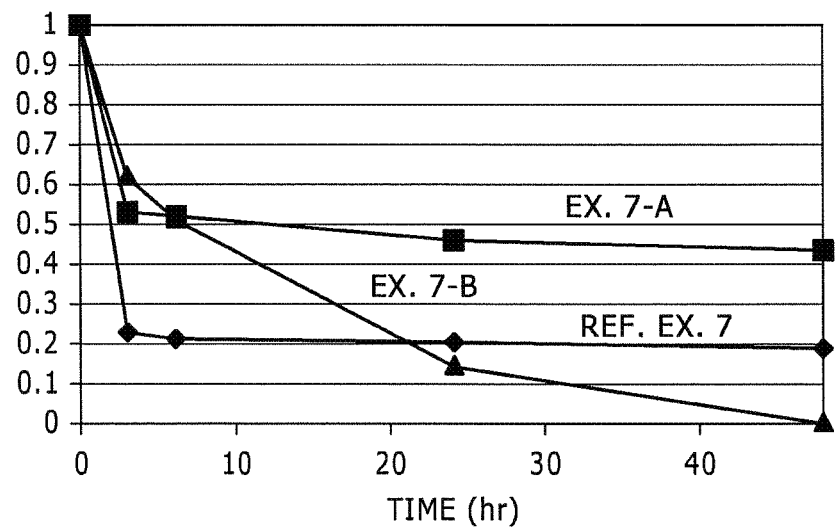
FIGS. 15(A) and 15(B) are a graph showing the results of assessments of changes with time in the degrees of decomposition of methyl orange when samples of Example 7-A and Example 7-B and Referential Example 7 were added to aliquots of an aqueous solution of methyl orange and the resulting mixtures were exposed to ultraviolet rays, and a graph showing the results of assessments of changes with time in the degrees of decomposition of a microcystin when a sample of Example 7-A and $TiO_2$ were added to aliquots of an aqueous solution of the microcystin and the resulting mixtures were exposed to ultraviolet rays.
Figure 15B:
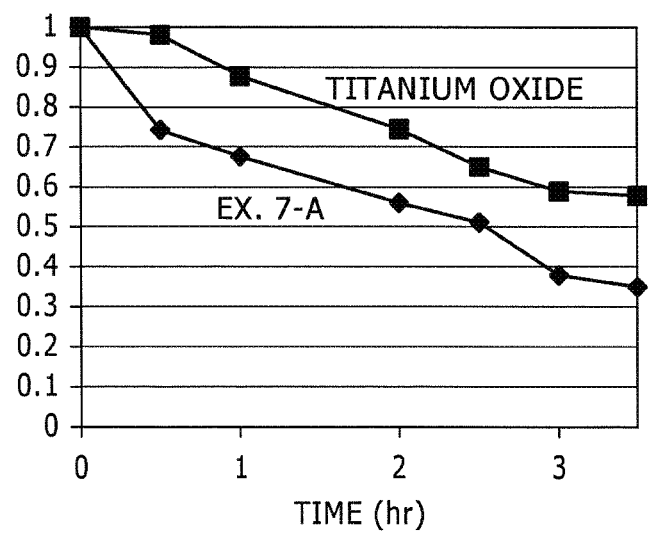

For assessments, portions (10 mg, each) of the samples of Examples 7-A and 7-B and Referential Example 7 were added to aliquots (50 mL) of a $3\times10^{-2}$ mol/L aqueous solution of methyl orange, respectively, followed by exposure to ultraviolet rays under 9-watt ultraviolet lamps (wavelength: 354 nm) to assess changes with time in the degree of decomposition of methyl orange (see (A) of FIG. 15). As a result, the rate of a decrease per hour was greatest in the first three hours, the decomposition of methyl orange in three hours from the initiation of the exposure was greatest in Referential Example 7, followed by Example 7-A and Example 7-B in this order. After an elapse of three hours from the initiation of the exposure, no decomposition of methyl orange, therefore, took place in Referential Example 7. In Examples 7-A and 7-B, on the other hand, it was found that the decomposition of methyl orange proceeded, and moreover, that the decomposition of methyl orange proceeded faster in Example 7-B in which the content of $TiO_2$ was high.

A portion (0.3 mg) of the sample of Example 7-A was added to an aliquot (10 mL) of a $1.5\times10^{-5}$ mol/L aqueous solution of a microcystin. For comparison, $TiO_2$ (0.3 mg) was added to another aliquot (10 mL) of the $1.5\times10^{-3}$ mol/L aqueous solution of the microcystin. The resultant mixtures were exposed to ultraviolet rays under 9-watt ultraviolet lamps (wavelength: 354 nm) to assess changes with time in the degree of decomposition of the microcystin (see (B) of FIG. 15). As a result, it has been found that the sample of Example 7-A decomposes microcystin more than $TiO_2$ alone. Similar results were obtained with a $1.0\times10^{-4}$ mol/L aqueous solution of the microcystin. These results are considered to be attributable to the formation of hole-electron pairs in the photocatalyst material by its exposure to ultraviolet rays and the oxidation and decomposition of the microcystin by such holes.

The porous carbon material in Example 7 is an environment compatible material derived from a natural product, and its microstructure can be obtained by treating and removing silicon components (oxidized silicon compounds), which are inherently contained in a plant-derived material as a raw material, with an acid or alkali. Therefore, its pores have sizes unrealizable with conventional activated carbon or sizes in a meso range (2 to 50 nm), and the array of pores still retains the bioregularity of the plant. In the composite photocatalyst material of Example 7, the photocatalyst material can be adhered on the porous carbon material extremely effectively owing to such a pore size and array, thereby making it possible to effectively induce decomposition by a photocatalytic effect. In the purification agent of Example 7, that is, an environment purification material, such a pore size and array is also considered to effectively act for the adsorption of a toxic substance, and at the same time, can cause the photocatalyst material to adhere on the porous material extremely effectively, thereby effectively inducing the decomposition and detoxification of a toxic substance by a photocatalytic effect. Moreover, the spreading of the toxic substance inside the purification agent can be promoted, thereby making it possible to more effectively induce the decomposition by the photocatalytic effect and to conduct the purification of water or the purification of air extremely effectively.

Example 8

Example 8 relates to the adsorbent according to the present invention. An adsorbent in Example 8 was composed of:

(A) a porous carbon material obtainable from a plant-derived material having a silicon content of 5 wt % or higher as a raw material, said porous carbon material having a silicon content of 1 wt % or lower, and (B) a magnetic material adhered on the porous carbon material.

The adsorbent had a specific surface area of 10 m²/g or greater as determined by the nitrogen BET method and a pore volume of 0.1 cm³/g or greater as determined by the BJH method and MP method. The adsorbent adsorbs microcystin LR (molecular weight: 994) thereon.

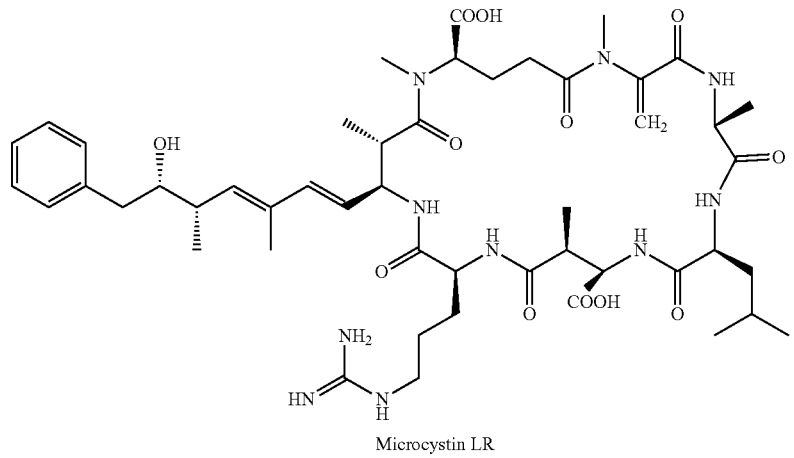

[Chem. 1]

Microcystin LR

The adsorbent in Example 8 was produced by a similar procedure as in Example 6. However, the time of production was different, and as will be shown below in Table 4, the value of its specific surface area, pore volume and saturation magnetization are slightly different from those of the adsorbent of Example 6.

Also employed as Referential Example 8 was activated carbon (product of Wako Pure Chemicals Industries, Ltd.), which will be shown below in Table 4.

In Example 8, a $1.0 \times 10^{-4}$ mol/L aqueous solution was prepared by using microcystin LR and purified water. The adsorbent of Example 8, which is shown in Table 4, was added in an amount of 0.25 g per mL of the prepared aqueous solution, followed by shaking at 25±2° C. for one hour. Subsequent to the shaking, the adsorbent was removed from the solution by using a membrane filter made of polytetrafluoroethylene and having a pore size of 500 μm. The absorbance of the filtrate was determined by UV-visible light absorbance measurement, and then, the molar concentration of the aqueous solution was determined. By comparing the molar concentration with the molar concentration of the initial aqueous solution before the adsorption, the adsorbed amount was calculated. The amount adsorbed per gram of the adsorbent was calculated based on the following equation. In Referential Example 8, the adsorbed amount was determined similarly.

(Amount adsorbed per gram of adsorbent)=(the molecular weight of solute)×{(the molar concentration of aqueous solution before adsorption)−(the molar concentration of aqueous solution after adsorption)}/(the amount of adsorbent per 1,000 mL)

TABLE 4

| Ex. | Ref. Ex. | BET specific surface area $m^2/g$ | Pore volume $cm^3/g$ | Adsorbed amount of microcystin mg | Saturation magnetization $A \cdot m^2/kg$ |
|---|---|---|---|---|---|
| 8 | | 472 | 0.4316 | 74.1 | 16.6 |
| | 8 | 1231 | 0.57 | 21.0 | 0.091 |

As is evident from Table 4, Example 8 is significantly greater in the adsorbed amount of microcystin LR compared with Referential Example 8. With the adsorbent of Example 8, the possession of magnetism made it possible to easily separate (remove) the adsorbent of Example 8 from water after it had been purified by using well-known water purification equipment of the magnetic separation system. When a magnetic material is caused to adhere on a porous carbon material as described above, the magnetic material is allowed to adhere in an increased amount per unit weight of the porous carbon material, thereby making it possible to obtain an adsorbent having excellent properties and high functionality, for example, an adsorbent which can be easily separated from water by magnetic separation equipment. As a consequence, microcystins contained as toxic components in water blooms, lake or marsh water, river water or the like can be adsorbed easily, surely and economically, and moreover, without causing secondary pollution of the environment and disturbing the environmental biosystem.

Example 9

Example 9 relates to the cosmetic according to the present invention. Cosmetics in Example 9 contained porous carbon material composites each composed of:

(A) a porous carbon material obtainable from a plant-derived material having a silicon content of 5 wt % or higher as a raw material, said porous carbon material having a silicon content of 1 wt % or lower, and (B) a metal-based material (a metal-based material capable of removing reactive oxygen, more specifically fine platinum particles or platinum nanoparticles in Example 9) adhered on the porous carbon material, wherein the porous carbon material composite had a specific surface area of 10 $m^2/g$ or greater as determined by the nitrogen BET method and a pore volume of 0.1 $cm^3/g$ or greater as determined by the BJH method and MP method.

In Example 9, the functional material was caused to adhere on the porous carbon material C described in Example 1. Described specifically, the complexing treatment was conducted as will be described hereinafter. To distilled water (182 mL), a 5 mmol aqueous solution of $H_2PtCl_6$ (8 mL) and L-ascorbic acid (surface protective agent; 3.5 mg) were added, and the resultant mixture was stirred for a while. Subsequently, the porous carbon material (0.43 g) was added. After exposed to ultrasonic waves for 20 minutes, a 40 mmol aqueous solution of $NaBH_4$ (10 mL) was added, followed by stirring for three hours. Subsequently, the mixture was filtered under suction to collect solid, and the solid was then dried at 120° C. to obtain the cosmetic of Example 9-A as a black powdery sample. As Example 9-B, a cosmetic was also prepared by a similar procedure as in Example 9-A except that L-ascorbic acid was not added.

Antioxidation properties of the thus-obtained cosmetics of Examples 9-A and 9-B were assessed by using 1,1-diphenyl-2-picrylhydrazyl (DPPH, number average molecular weight: 394) as stabilizing radicals. Specifically, a $1.0 \times 10^{-4}$ mol solution of DPPH in ethanol was prepared. To aliquots of the thus-prepared solution of DPPH, the cosmetics of Examples 9-A and 9-B were added, respectively, as much as 2.5 μg per mL of the solution of DPPH, and the resulting mixtures were shaken at 25±2° C. Using membrane filters having 200-nm pores, the cosmetics were filtered off from the respective solutions. The absorbances of the respective filtrates were determined by UV-visible light absorbance measurement. By comparing the absorbances with the initial absorbance before the adsorption, the percent residues of DPPH radicals were calculated. As Comparative Example 9-A, samples (Comparative Examples 9-A and 9-B) were also prepared as in Examples 9-A and 9-B by using commercially-available activated carbon as a carbon material, and the percent residues of DPPH radicals were assessed.

In Table 5, the specific surface areas and pore volumes in Examples 9-A and 9-B and Comparative Examples 9-A and 9-B are shown together, and the platinum contents of the respective samples as determined by ICP emission analyses are also shown. The results of X-ray diffraction of the respective samples as obtained by the powder X-ray diffraction method are shown in FIG. 16.

TABLE 5

| | Specific surface area $(m^2/g)$ | Pore volume $(cm^3/g)$ | Platinum content (wt %) |
|---|---|---|---|
| Ex. 9-A | 1165 | 1.04 | 0.357 |
| Ex. 9-B | 852 | 0.86 | 0.413 |
| Comp. Ex. 9-A | 1028 | 0.62 | 0.329 |
| Comp. Ex. 9-B | 857 | 0.49 | 0.320 |

Figure 16:
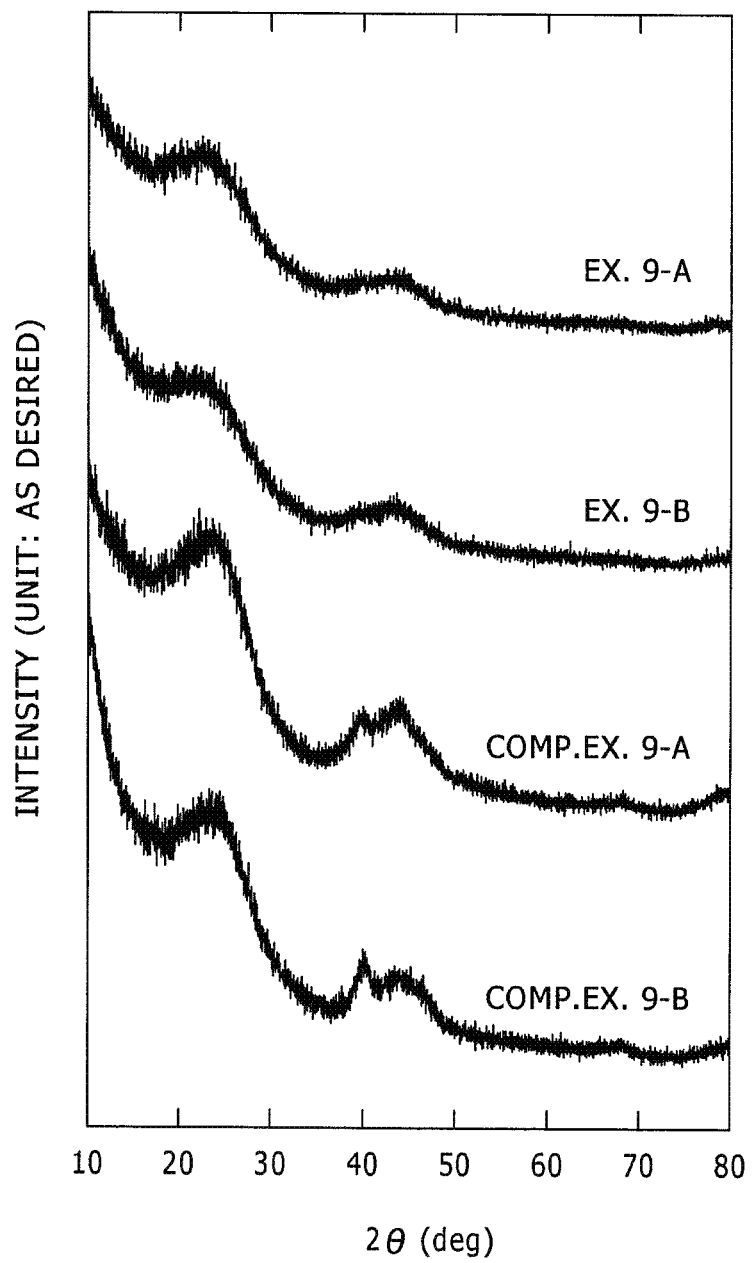
FIG. 16 is a chart of the results of X-ray diffraction of Example 9-A, Example 9-B, Comparative Example 9-A and Comparative Example 9-B as obtained by powder X-ray diffractometry.

In the X-ray diffraction patterns of the respective samples shown in FIG. 16, diffraction peaks from the (111) plane of Pt are observed around 2θ=40° on the respective specimens. It is, therefore, envisaged that platinum was deposited. Further, the diffraction peak of platinum becomes shaper in the order of Example 9-A, Example 9-B, Comparative Example 9-A and Comparative Example 9-B, thereby suggesting that the particle size of fine platinum particles differs in the respective samples. From these findings, it is also conceivable that the use of a porous carbon material can facilitate the formation of fine platinum particles of relatively small particle size, and further, that the use of ascorbic acid as a surface protective agent can further inhibit the grain growth of fine platinum particles. In (A) of FIG. 17 and (B) of FIG. 17, electron micrographs of Example 9-A and Comparative Example 9-A are shown. As predicted from the X-ray diffraction patterns, it is envisaged that the fine platinum particles (platinum nanoparticles) deposited on the porous carbon material are far smaller compared with those deposited on the activated carbon (Comparative Example 9-A). This difference is considered to be attributable to the microstructure and surface conditions characteristic to the porous carbon material derived from rice husks.

FIG. 18 shows changes with time in the percent residue of radicals. In Examples 9-A and 9-B, the fine platinum particles, irrespective of the presence or absence of ascorbic acid, captured DPPH and removed radicals substantially completely in from 40 minutes to 50 minutes or so. In Comparative Examples 9-A and 9-B, on the other hand, a difference was recognized, depending on the presence or absence of ascorbic acid, in the time required for the removal of radicals.

The porous carbon material in Example 9 is an environment compatible material derived from a natural product, and its microstructure can be obtained by treating and removing silicon components (oxidized silicon compounds), which are inherently contained in a plant-derived material as a raw material, with an acid or alkali. Therefore, its pores have sizes unrealizable with conventional activated carbon or sizes in a meso range (2 to 50 nm), and the array of pores still retains the bioregularity of the plant. In the cosmetic of Example 9, the platinum-based material or the like can be carried on the porous carbon material extremely effectively owing to such a pore size and array. It is, therefore, unnecessary to use a protective colloid agent, for example, for forming fine platinum particles of nanosize into a colloid. Further, the fine platinum particles are not covered with the protective colloid agent, thereby making it possible to exhibit a high antioxidation effect against reactive oxygen species such as superoxides, hydroxy radicals, hydrogen peroxide and singlet oxygen which are considered to be causes of acute inflammatory, tissue damage and aging. Accordingly, a so-called anti-aging effect can be obtained.

Example 10

Example 10 is also a modification of Example 1. In porous carbon material composites of Example 10, functional materials are composed of external stimulus responsive substances and releasable substances. It is to be noted that in Example 10, the porous carbon material C described in Example 1 was used.

Figure 19:
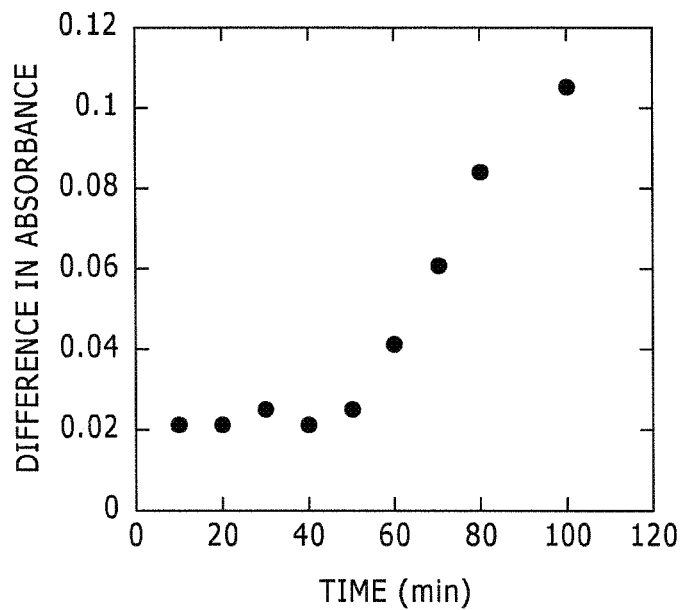
FIG. 19 is a graph showing the results of a study on changes with time in absorbance at 605 nm when the porous carbon material composite of Example 10 was exposed to ultraviolet rays of 365 nm while using alizarin green G as a releasable substance.

In Example 10, light was used as a physical external stimulus, and azobenzene or coumarin was used as external stimulus responsive substance, that is, as a light responsive substance. Responsive to light, azobenzene transitions between cis and trans conformations. As a result, the releasable substance can be released. On the other hand, coumarin changes into a dimer in response to light, and as a result, the releasable substance can be released. FIG. 19 shows the results of a study on changes with time in absorbance at 605 nm when for a test, alizarin green G was used as the releasable substance and ultraviolet rays of 365 nm were irradiated. It is to be noted that FIG. 19 shows a difference from the absorbance at 605 nm of the sample when not exposed to ultraviolet rays of 365 nm. It is envisaged that, when exposed to ultraviolet rays of 365 nm, alizarin green G was released and its released amount increased with time.

Figure 20:
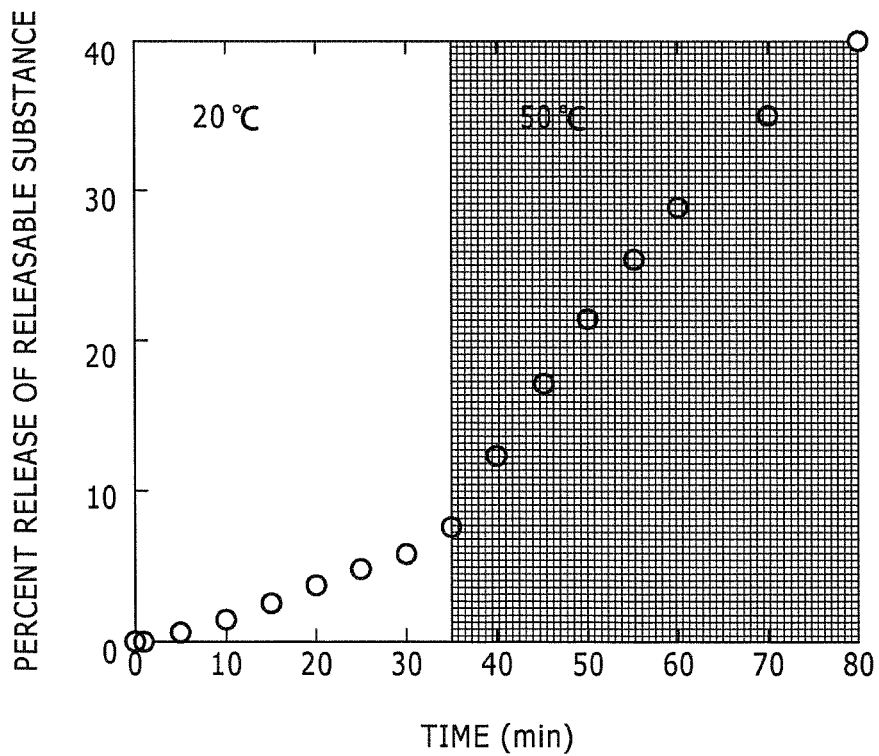
FIG. 20 is a graph showing the results of a study by the absorbance at 605 nm on the degree of temperature-dependent release of a releasable substance from the porous carbon material composite of Example 10 while using alizarin green G as the releasable substance.

As an alternative, temperature was used as a physical external stimulus, and poly-N-isopropylacrylamide (IPAAm) or polyethylene oxide (for example, polyethylene oxide having a molecular weight of from 1,000 to 2,000, PEO 1000-2000) was used as external stimulus responsive substance, that is, as a temperature responsive substance. FIG. 20 shows the results of a study based on absorbance at 605 nm on the degree of release of a releasable substance at varied temperatures when for a test, alizarin green G was used as the releasable substance and IPAAm was used as a temperature responsive substance. Until the 35th minute from the initiation of the test, the atmospheric temperature was controlled at 20° C. Upon elapsed time of 35 minutes from the initiation of the test, the atmospheric temperature was raised to 50° C. As a result, the degree of release (the amount released per unit time) of alizarin green G became clearly different by the change in the atmospheric temperature. This difference is considered to be attributable to a contraction of each IPAAm molecule at 50° C. so that a sort of spacing was formed to permit the release of alizarin green G.

Figure 21:
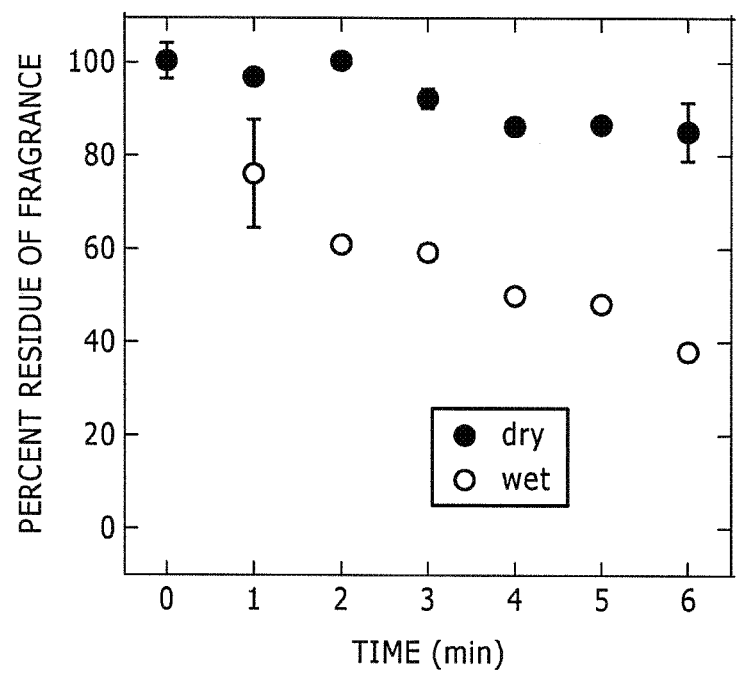
FIG. 21 is a graph showing the results of a study on the degree of humidity-dependent release of a releasable substance from the porous carbon material composite of Example 10 while using limonene as the releasable substance.

As a further alternative, FIG. 21 shows the results of a study on the degree of humidity-dependent release of a releasable substance when humidity was used as a physical external stimulus, polyethylene glycol (molecular weight: 1,540) was used as an external stimulus responsive substance, i.e., as a humidity responsive material, and for the test, a fragrance, i.e., limonene was used as the releasable substance. In FIG. 21, the dots indicate data at a temperature of 40° C. (a constant-temperature chamber was used) while the circles indicate data at a temperature of 40° C. and a humidity of 98%. It is envisaged that the amount of released limonene differed depending on humidity.

As described above, it is possible in Example 10 to control a change in the structure of the external stimulus responsive substance by an external stimulus, and further, to control the desorption of the releasable substance, which is adhered, bound, adsorbed or carried on the porous carbon material, from the porous carbon material. The porous carbon material in Example 10 has pores of sizes unrealizable with conventional activated carbon or sizes in a meso range (2 to 50 nm), can sufficiently reflect a change that takes place when the external stimulus responsive substance responds to an external stimulus, and based on this change, can release the releasable substance.

Example 11

Example 11 is also a modification of Example 1. In porous carbon material composites of Example 11, functional materials are composed of components having a moisturizing effect and/or an antioxidation effect, specifically active ingredients contained in cosmetic waters, that is, Trolox, astaxanthin and coenzyme Q10 shown below. In addition, a measurement was also conducted on daidzein, which is a cosmetic ingredient and is a substance having a hydrophobic beauty component.

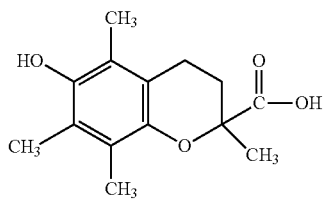
Trolox

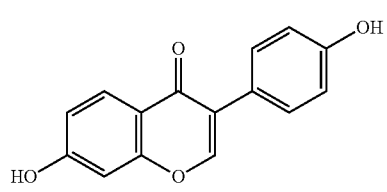
Daidzein

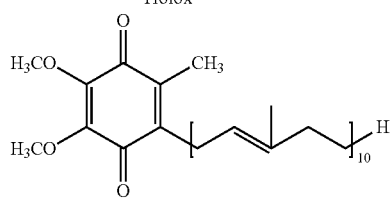
Coenzyme Q10

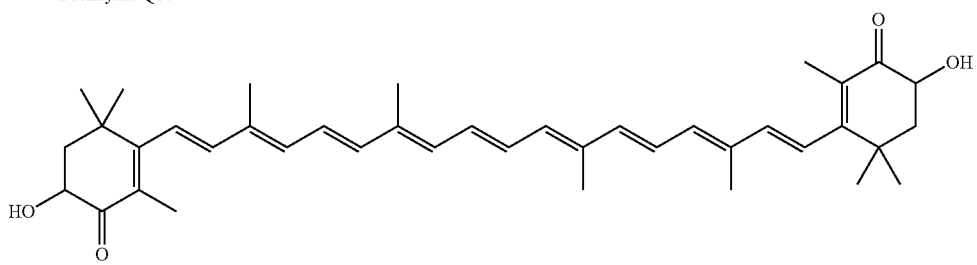
Astaxanthin

Measurements were conducted to determine how much Trolox (number average molecular weight: 250), daidzein (number average molecular weight: 254), astaxanthin (number average molecular weight: 596) and coenzyme Q10 (number average molecular weight: 1,002) the porous carbon material C would adsorb, using the porous carbon material C explained in Example 1 as the porous carbon material. Solutions of the concentrations shown below in Table 6 were prepared. It is to be noted that the concentrations of the respective solutions before adsorption were set as desired. The samples shown in Table 7 (0.010 g each) were separately added to aliquots (40.0 mL each) of the thus-prepared solution, followed by shaking at 37±2° C. for one hour. Subsequent to the shaking, the porous carbon material composites were separately removed from the aliquots of the solution by using membrane filters made of polytetrafluoroethylene and having a pore size of 500 nm. The absorbances of the respective filtrates were determined by UV-visible light absorbance measurement, and then, the molar concentrations of the respective solutions were determined. By comparing the molar concentrations with the molar concentrations of the corresponding initial solutions before the adsorption, the adsorbed amounts were calculated. Each amount adsorbed per gram of the porous carbon material was calculated based on the equation described in Example 1 and used to determine the adsorbed amount per gram of the porous carbon material. The results are shown in FIG. 8.

TABLE 6

| Solute | Molecular weight of solute | Molar concentration |
|---|---|---|
| Solution 11-A | Trolox | 250 | $8.01 \times 10^{-4}$ |
| Solution 11-B | Daidzein | 254 | $2.99 \times 10^{-4}$ |
| Solution 11-C | Astaxanthin | 596 | $3.81 \times 10^{-5}$ |
| Solution 11-D | Coenzyme Q10 | 1,002 | $1.98 \times 10^{-4}$ |

TABLE 7

| | Product name | Manufacturer | Specific surface area ($m^2/g$) | Pore volume ($cm^3/g$) |
|---|---|---|---|---|
| Example 11 | | | 1,309 | 1.16 |
| Referential Example 11-A | Activated carbon | Wako Pure Chemical Industries, Ltd. | 1,231 | 0.57 |
| Referential Example 11-B | Medical charcoal | Horie Shoyaku Co., Ltd. | 924 | 0.70 |
| Referential Example 11-C | Medical charcoal | Oriental Pharmaceutical Co., Ltd. | 928 | 0.76 |

TABLE 8

| | Trolox | Daidzein | Astaxanthin | Coenzyme Q10 |
|---|---|---|---|---|
| Example 11 | 210.3 | 108.8 | 16.15 | 216.4 |
| Referential Example 11-A | 66.8 | 64.5 | | |

TABLE 8-continued

|  | Trolox | Daidzein | Astaxanthin | Coenzyme Q10 |
|---|---|---|---|---|
| Referential Example 11-B | 39.9 | 74.1 | 8.97 | 145.3 |
| Referential Example 11-C | 43.5 | 76.7 | 10.22 | 157.0 |

It is appreciated from Table 8 that in the porous carbon material composites of Example 11, the components having a moisturizing effect and/or an antioxidation effect or the cosmetic ingredients were held and carried in sufficient amounts.

The present invention has been described based on the preferred examples. It should, however, be borne in mind that the present invention are not limited to these examples and various modifications are feasible. In the examples, the description was made using rice skulls as a raw material for the porous carbon material. However, other plants may also be used as raw materials. Examples of such other plants can include straws; reed; seaweed stems; vascular plants, ferns and mosses which grow on land; algae; and seaweeds. These materials may be used singly, or plural ones of them may be used in combination.

Specifically, the porous carbon material can be obtained, for example, by using straws of a rice plant (for example, grown in Kagoshima Prefecture; Isehikari) as a raw material, that is, a plant-derived material, carbonizing the straws as the raw material into a carbonaceous material (porous carbon material precursor), and then applying an acid treatment. As an alternative, the porous carbon material can also be obtained by using grass reed as a raw material, that is, a plant-derived material, carbonizing the grass reed as the raw material into a carbonaceous material (porous carbon material precursor), and then applying an acid treatment. It is to be noted that a similar process as in any one of Examples 1 to 8 can be employed for the production of the porous carbon material composites.

As a further alternative, the porous carbon material can also be obtained by using seaweed stems (grown in the Sanriku district of Iwate Prefecture) as a raw material, that is, as a plant-derived material, carbonizing the seaweed stems as the raw material into a carbonaceous material (porous carbon material precursor), and then applying an acid treatment. Specifically, the seaweed stems were first heated, for example, at a temperature of 500° C. or so to char the same. It is to be noted that before the heating, the seaweed stems as a raw material may be treated with an alcohol. As a specific treatment method, the method that immerses the seaweed stems in ethyl alcohol or the like can be mentioned. By this treatment, the water contained in the raw material can be decreased, and at the same time, non-carbon elements and mineral components which would be contained in a porous carbon material to be obtained finally can be dissolved out. By this alcohol treatment, it is also possible to reduce the occurrence of gas during carbonization. More specifically, the seaweed stems are immersed for 48 hours in ethyl alcohol. It is to be noted that ultrasonication may preferably be applied in ethyl alcohol. Next, the seaweed stems are heated and charred at 500° C. for five hours in a nitrogen gas stream to obtain a charred material. It is to be noted that by conducting such a treatment (precarbonization treatment), tar components which would be formed in the subsequent carbonization can be decreased or eliminated. Subsequently, the charred material (10 g) is placed in an alumina-made crucible, and is heated to 1,000° C. at a ramp-up rate of 5° C./min in a nitrogen gas stream (10 L/min). The charred material is then carbonized at 1,000° C. for five hours into a carbonaceous material (porous carbon material precursor), which is thereafter allowed to cool down to room temperature. It is to be noted that during the carbonization and cooling, nitrogen gas should be caused to flow continuously. The porous carbon material precursor is then immersed overnight in a 46 vol % aqueous solution of hydrofluoric acid to conduct its acid treatment, followed by washing with water and ethyl alcohol until pH 7 is reached. By finally conducting drying, it is possible to obtain a porous carbon material. Subsequently, the complexing treatment and activation treatment described in any one of Examples 1 to 6 can be applied.

It is to be noted that in the porous carbon material composite according to the present invention, the porous carbon material itself has ability to adsorb substances. The porous carbon material composite according to the present invention can also be used as a carrier for carrying a drug thereon or as a drug-release sustaining agent. From the porous carbon material composite according to the present invention, a sheet-shaped member can also be produced, or an adsorbing sheet formed of a support member with the sheet-shaped member held thereon can also be formed. In addition, the porous carbon material composite according to the present invention can also be used as an orally-administrable adsorbent preparation or as a material for functional foods. In these applications, suitable functional materials can be chosen, as desired, depending on the properties required for the porous carbon material composites.

Described specifically, the porous carbon material composite according to the present invention can be used to selectively adsorb various unnecessary molecules in the body. That is, the porous carbon material composite according to the present invention can be used as orally-administrable adsorbent preparations or medical adsorbent preparations for internal medicines useful for the treatment and prevention of diseases. When the porous carbon material composite according to the present invention is applied to the field of orally-administrable adsorbent preparations or medical adsorbent preparations, it can be used as an adsorbent for adsorbing indole, an adsorbent for adsorbing creatinine, an adsorbent for adsorbing uric acid, an adsorbent for adsorbing adenosine, an adsorbent for adsorbing alizarin cyanine green, an adsorbent for adsorbing lysozyme, an adsorbent for adsorbing α-amylase, an adsorbent for adsorbing albumin, an adsorbent for adsorbing 3-methylindole (skatole), an adsorbent for adsorbing tryptophan, an adsorbent for adsorbing indican, an adsorbent for adsorbing thoeophyline, an adsorbent for adsorbing inosine 5-monophosphate disodium salt, an adsorbent for adsorbing adenosine 5-triphosphate disodium salt, and adsorbent for adsorbing organic substances (for example, organic molecules or proteins) having number average molecular weights of from $1 \times 10^2$ to $1 \times 10^5$, organic substances (for example, organic molecules or proteins) having number average molecular weights of preferably from $1 \times 10^2$ to $5 \times 10^4$, more preferably from $1 \times 10^2$ to $2 \times 10^4$, still more preferably from $1 \times 10^2$ to $1 \times 10^4$. Further, substances to be adsorbed can include water-soluble, basic or amphoteric substances such as ammonia, urea, dimethylamine, guanidine compounds such as methylguanidine, sulfur-containing amino acids, phenol, p-cresol, oxalic acid, homocysteine, guanidinosuccinic acid, myoinositol, indoxyl sulfate, pseudouridine, cyclic adenosine monophosphate, β-aminoisobutyric acid, octopamine, α-aminoisobutyric acid, parathyroid hormone, β2-microglobulin, ribonuclease, natriuretic hormone, aspartic acid, and arginine. Also included can be purine and purine derivatives, adenine and guanine as purine bases, guanosine and inosine as purine nucleosides, and adenylic acid, guanylic acid and inosinic acid as purine nucleotides. Further included can be oligonucleotides and polynucleotides as low-molecular and high-molecular nucleic acids. Still further included can be polyamines, 3-deoxyglucosone, various peptide hormones, granulocyte inhibitory proteins (GIPs), degranulocyte inhibitory proteins (DIPs), and chemotaxis inhibitory proteins. Even still further included can be carbamylated hemoglobin, glycation end products, granulocyte/monocyte function inhibitors, oxidation promoters, and the like. The porous carbon material composite according to the present invention can also be used as a packing material (absorbent) for blood purification columns. In addition, the porous carbon material composite according to the present invention can also be applied to adsorbing sheets. Specifically, such adsorbing sheets can each be designed in a form that it is composed of a sheet-shaped member, which includes the porous carbon material composite according to the present invention, and a support member holding the sheet-shaped member thereon. Furthermore, the porous carbon material composite according to the present invention can also be used as a water-purifying adsorbent for purifying water. It is to be noted that a chemical treatment or molecule modification may be applied to the surfaces of the porous carbon material composite according to the present invention. The chemical treatment can be, for example, a treatment that forms carboxyl groups on the surfaces by treatment with nitric acid. A molecule modification is also feasible by chemically reacting the porous carbon material with a chemical species or protein having one or more reactable hydroxyl groups, carboxyl groups, amino groups and/or the like. In these applications, suitable functional materials can be chosen, as desired, depending on the properties required for the porous carbon material composites.

As drugs which can be adsorbed and carried on the porous carbon material composite according to the present invention, organic molecules, polymer molecules and proteins can be mentioned. Specific examples can include, but are not limited to, pentoxifylline, prazosin, acyclovir, nifedipine, diltiazem, naproxen, ibuprofen, flurbiprofen, ketoprofen, fenoprofen, indomethacin, diclofenac, fentiazac, estradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-asa, quinidine, perindopril, morphine, pentazocine, paracetamol, omeprazole, metoclopramide, aspirin, and metformin; and from the viewpoint of systemic and topical treatments, various hormones (for example, insulin, estradiol, and the like), asthma remedies (for example, albuterol), tuberculosis remedies (for example, rifanpicin, ethambutol, streptomycin, isoniazid, pyrazinamide, and the like), cancer remedies (for example, cisplatin, carboplatin, Adriamycin, 5-FU, paclitaxel, and the like), and hypertension remedies (for example, clonidine, prazosin, propranolol, labetalol, bunitrolol, reserpine, nifedipine, furosemide, and the like). A porous carbon material composite-drug complex can be obtained by dissolving such a drug in an organic solvent which can dissolve the drug, immersing the porous carbon material composite according to the present invention in the resultant solution, and then eliminating the solvent and any extra solute. Specific solvents can include water, methyl alcohol, ethyl alcohol, isopropyl alcohol, butyl alcohol, acetone, ethyl acetate, chloroform, 2-chloromethane, 1-chloromethane, hexane, tetrahydrofuran, pyridine, and the like. As the drug in a sustained release drug, ibuprofen can be mentioned. In these applications, suitable functional materials can be chosen, as desired, depending on the properties or the like required for the porous carbon material composites. Further, the material adapted to permit the adhesion of a functional material, which is composed of an external stimulus responsive substance and a releasable substance, thereon can be changed from the porous carbon material, for example, to the porous carbon material disclosed in Japanese Patent Laid-open No. 2005-262324 and including pores having three-dimensional regularity or to fine silica particles.

What is claimed is:

1. A process for producing a porous carbon material composite, the process comprising:
    carbonizing a silicon-containing plant-derived material at from 800° C. to 1,400° C. and generating a precursor carbonized material with oxidized silicon compounds;
    reducing the silicon in the precursor carbonized material by treating the carbonized material with a hydrofluoric acid or an alkali and removing the oxidized silicon compounds;
    activating the precursor carbonized material after reducing the silicon in the precursor carbonized material by subjecting the precursor carbonized material to a steam stream and generating a porous carbon material; and
    causing a functional material to adhere on the porous carbon material using a complexing treatment in which the porous carbon material is (a) immersed at 25° C. for 24 hours in a 0.5 mol/L aqueous solution of iron chloride, (b) then washed with water and, (c) then subjected to heat treatment at 750° C. for three hours in a nitrogen atmosphere to complete the creation of the porous carbon material composite.

2. The process of claim 1, comprising activating the precursor carbonized material by subjecting the precursor carbonized material to the steam stream for at least two hours, the steam being at a temperature of 900 degrees Centigrade.

3. The process of claim 1, comprising reducing the silicon in the precursor carbonized material by treating the carbonized material with the hydrofluoric acid.

4. The process for producing the porous carbon material composite according to claim 1, wherein:
    the plant-derived material has a silicon content of 5 wt % or higher;
    the porous carbon material has a silicon content of 1 wt % or lower; and
    the porous carbon material composite has a specific surface area of 10 m2/g or greater as determined by the nitrogen BET method and a pore volume of 0.1 cm3/g or greater as determined by the BJH method and the MP method.

5. The process of claim 1, wherein:
    the porous carbonized material has a cumulative pore volume of at least 0.18 cm3/g for pores sized 5 nm or greater,
    the functional material is in a form of fine particles, thin films, or sea islands,
    the functional material is dissimilar to the porous carbonized material, and
    the porous carbonized material does not contain silicon carbide.

6. The process of claim 1, wherein the functional material is titanium oxide or zinc oxide.

7. The process of claim 1, wherein the functional material is cadmium sulfide, lead sulfide, cadmium selenide, lead selenide, zinc selenide, indium arsenide, gallium arsenide, indium phosphide, gallium phosphide, gallium antimonide, indium antimonide, or lanthanide oxide.

8. The process of claim 1, wherein the porous carbonized material has a specific surface area of 50 m2/g or greater as determined by the nitrogen BET method.

9. The process of claim 1, wherein the porous carbonized material has a specific surface area of 100 m2/g or greater as determined by the nitrogen BET method.

10. The process of claim 1, wherein the porous carbonized material has a specific surface area of 400 m2/g or greater as determined by the nitrogen BET method.

11. The process of claim 1, wherein the porous carbonized material has a cumulative pore volume of 0.1 cm3/g or greater as determined by the BJH method and the MP method.

12. The process of claim 1, wherein the porous carbonized material has a cumulative pore volume of 0.3 cm3/g or greater as determined by the BJH method and the MP method.

13. The process of claim 1, wherein the plant-derived material is rice husk.

14. The process of claim 1, wherein the plant-derived material has a silicon content of 5 wt % or greater.

15. The process of claim 1, wherein the functional material exhibits surface plasmon absorption or light absorption by a semiconductor.

16. The process of claim 1, wherein the functional material is a magnetic material.

17. The process of claim 1, wherein the functional material is composed of a noble metal, noble metal alloy, oxide semiconductor or compound semiconductor.

18. The process of claim 1, wherein the functional material is composed of a component having a moisturizing effect and/or antioxidant effect.

* * * * *